(12) United States Patent
Meheus et al.

(10) Patent No.: US 6,362,007 B1
(45) Date of Patent: Mar. 26, 2002

(54) METHYLATED, SMD HOMOLOGOUS PEPTIDES, REACTIVE WITH THE ANTIBODIES FROM SERA OF LIVING BEINGS AFFECTED WITH SYSTEMIC LUPUS ERYTHEMATOSUS

(75) Inventors: Lydie Meheus, Merelbeke; Ann Union, Aalter; Joseph Raymackers, Eke, all of (BE); Reinhard Georg Lührmann, Marburg (DE)

(73) Assignee: Innogenetics N.V., Ghent (BE)

( * ) Notice: Subject to any disclaimer, the term of this patent is extended or adjusted under 35 U.S.C. 154(b) by 0 days.

(21) Appl. No.: 09/297,981

(22) PCT Filed: Aug. 31, 1998

(86) PCT No.: PCT/EP98/05518

§ 371 Date: May 10, 1999

§ 102(e) Date: May 10, 1999

(87) PCT Pub. No.: WO99/11667

PCT Pub. Date: Mar. 11, 1999

(30) Foreign Application Priority Data

Aug. 29, 1997 (EP) ............................................. 97870127

(51) Int. Cl.[7] ........................................... G01N 33/514
(52) U.S. Cl. ..................... 436/506; 436/518; 530/324
(58) Field of Search .................. 424/185.1; 514/12; 530/324; 436/506, 518

(56) References Cited

U.S. PATENT DOCUMENTS

| 5,407,833 A | 4/1995 | Van Regenmortel et al. .... 436/508 |
| 5,945,105 A | * 8/1999 | Hiepe et al. ............. 424/185.1 |

FOREIGN PATENT DOCUMENTS

| WO | 86/01210 | 2/1986 |
| WO | 91/18920 | 12/1991 |
| WO | 95/13805 | 5/1995 |

OTHER PUBLICATIONS

Rokeach, L.A. et al., "Mapping of the Immunoreactive Domains of a Small Nuclear Ribonucleoprotein–Associated Sm–D Autoantigen," *Clinical Immunology and Immunopathology* 35:35–15–324 (1992).

Luis A. Rokeach, et al, "Molecular cloning of a cDNA enclocding the human Sm–D autoantigen", *Proc. Natl. Acad. Sci, USA*, vol. 85, (Jul. 1988) pp. 4832–4836.

Nenoon Rawal, et al, "Structural specificity of substrate for S–adensylmethionine: protein arginine N–methyltransferases", *Biochimica et Biophysica Acta* 1248 (1995) pp. 11–18.

International Search Report on PCT/EP98/05518 dated Jan. 6, 1999.

* cited by examiner

*Primary Examiner*—Donna C. Wortman
*Assistant Examiner*—Robert A. Zeman
(74) *Attorney, Agent, or Firm*—Howrey Simon Arnold & White, LLP

(57) ABSTRACT

The present invention relates to a method of producing certain peptides containing methylated arginines that are followed by a glycine residue and that constitute immunogenic determinants of antibodies present in sera from patients with systemic lupus erythematosus, or Epstein-Barr virus and wherein the methylation is a prerequisite for reacting with said antibodies. The invention also relates to the use of said peptides for diagnosis and treatment of systemic lupus erythematosus and related diseases, and diseases in which Epstein-Barr virus has been implicated.

9 Claims, 3 Drawing Sheets

SEQUENCE LISTING

```
<160> NUMBER OF SEQ ID NOS: 30

<210> SEQ ID NO 1
<211> LENGTH: 19
<212> TYPE: PRT
<213> ORGANISM: Artificial Sequence
<220> FEATURE:
<221> NAME/KEY: PEPTIDE
<222> LOCATION: (2)..(18)
<223> OTHER INFORMATION: "Xaa" STANDS FOR A MONO- OR DIMETHYLATED
      ARGININE
<220> FEATURE:
<223> OTHER INFORMATION: Description of Artificial Sequence: Synthetic

<400> SEQUENCE: 1

Gly Xaa Gly Xaa Gly Xaa Gly Xaa Gly Xaa Gly Xaa Gly Xaa Gly Xaa
 1               5                  10                  15

Gly Xaa Gly

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: PEPTIDE
<222> LOCATION: (2)..(10)
<223> OTHER INFORMATION: "Xaa" STANDS FOR A MONO- OR DIMETHYLATED
      ARGININE

<400> SEQUENCE: 2

Ala Xaa Gly Xaa Gly Xaa Gly Met Gly Xaa Gly
 1               5                  10

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: PEPTIDE
<222> LOCATION: (7)..(15)
<223> OTHER INFORMATION: "Xaa" STANDS FOR A MONO- OR DIMETHYLATED
      ARGININE

<400> SEQUENCE: 3

Lys Ala Gln Val Ala Ala Xaa Gly Xaa Gly Xaa Gly Met Gly Xaa Gly
 1               5                  10                  15

Asn

<210> SEQ ID NO 4
<211> LENGTH: 38
```

```
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: PEPTIDE
<222> LOCATION: (17)..(33)
<223> OTHER INFORMATION: "Xaa" STANDS FOR A MONO- OR DIMETHYLATED
      ARGININE

<400> SEQUENCE: 4

Asp Val Glu Pro Lys Val Lys Ser Lys Lys Arg Glu Ala Val Ala Gly
 1               5                  10                  15

Xaa Gly Xaa Gly Xaa Gly Xaa Gly Xaa Gly Xaa Gly Xaa Gly Xaa Gly
             20                  25                  30

Xaa Gly Gly Pro Arg Arg
         35

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: PEPTIDE
<222> LOCATION: (5)..(13)
<223> OTHER INFORMATION: "Xaa" STANDS FOR A MONO- OR DIMETHYLATED
      ARGININE

<400> SEQUENCE: 5

Asp Asn His Gly Xaa Gly Xaa Gly Xaa Gly Xaa Gly Xaa Gly Gly Gly
 1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: PEPTIDE
<222> LOCATION: (3)..(13)
<223> OTHER INFORMATION: "Xaa" STANDS FOR A MONO- OR DIMETHYLATED
      ARGININE

<400> SEQUENCE: 6

Gly Gly Xaa Gly Xaa Gly Gly Ser Gly Gly Xaa Gly Xaa Gly Gly
 1               5                  10                  15

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: PEPTIDE
<222> LOCATION: (4)..(10)
<223> OTHER INFORMATION: "Xaa" STANDS FOR A MONO- OR DIMETHYLATED
      ARGININE

<400> SEQUENCE: 7

Glu Arg Ala Xaa Gly Xaa Gly Xaa Gly Xaa Gly Glu
 1               5                  10

<210> SEQ ID NO 8
<211> LENGTH: 46
<212> TYPE: PRT
```

```
<213> ORGANISM: Artificial Sequence
<220> FEATURE:
<223> OTHER INFORMATION: Description of Artificial Sequence: Synthetic
<220> FEATURE:
<221> NAME/KEY: PEPTIDE
<222> LOCATION: (6)..(44)
<223> OTHER INFORMATION: "Xaa" STANDS FOR A MONO- OR DIMETHYLATED
      ARGININE

<400> SEQUENCE: 8

Gly Gly Gln Gln Asp Xaa Gly Gly Xaa Gly Xaa Gly Gly Gly Gly
 1               5                  10                  15

Tyr Asn Xaa Ser Ser Gly Gly Tyr Glu Pro Xaa Gly Xaa Gly Gly
             20                  25                  30

Xaa Gly Gly Xaa Gly Gly Met Gly Gly Ser Asp Xaa Gly Gly
         35                  40                  45

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: PEPTIDE
<222> LOCATION: (6)..(11)
<223> OTHER INFORMATION: "Xaa" STANDS FOR A MONO- OR DIMETHYLATED
      ARGININE

<400> SEQUENCE: 9

Gly Gly Gln Gln Asp Xaa Gly Gly Xaa Gly Xaa Gly Gly Gly Gly
 1               5                  10                  15

Tyr Asn

<210> SEQ ID NO 10
<211> LENGTH: 26
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: PEPTIDE
<222> LOCATION: (7)..(24)
<223> OTHER INFORMATION: "Xaa" STANDS FOR A MONO- OR DIMETHYLATED
      ARGININE

<400> SEQUENCE: 10

Ser Gly Gly Tyr Glu Pro Xaa Gly Xaa Gly Gly Xaa Gly Gly Xaa
 1               5                  10                  15

Gly Gly Met Gly Gly Ser Asp Xaa Gly Gly
             20                  25

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: PEPTIDE
<222> LOCATION: (4)..(15)
<223> OTHER INFORMATION: "Xaa" STANDS FOR A MONO- OR DIMETHYLATED
      ARGININE

<400> SEQUENCE: 11

Asp Phe Asn Xaa Gly Gly Gly Asn Gly Xaa Gly Gly Xaa Gly Xaa Gly
 1               5                  10                  15
```

Gly

<210> SEQ ID NO 12
<211> LENGTH: 29
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: PEPTIDE
<222> LOCATION: (4)..(21)
<223> OTHER INFORMATION: "Xaa" STANDS FOR A MONO- OR DIMETHYLATED ARGININE

<400> SEQUENCE: 12

Asp Phe Asn Xaa Gly Gly Gly Asn Gly Xaa Gly Gly Xaa Gly Xaa Gly
 1               5                  10                  15

Gly Pro Met Gly Xaa Gly Gly Tyr Gly Gly Gly Gly Ser
             20                  25

<210> SEQ ID NO 13
<211> LENGTH: 38
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: PEPTIDE
<222> LOCATION: (4)..(34)
<223> OTHER INFORMATION: "Xaa" STANDS FOR A MONO- OR DIMETHYLATED ARGININE

<400> SEQUENCE: 13

Gly Asp Asp Xaa Xaa Gly Xaa Gly Gly Tyr Asp Xaa Gly Gly Tyr Xaa
 1               5                  10                  15

Gly Xaa Gly Gly Asp Xaa Gly Gly Phe Xaa Gly Gly Xaa Gly Gly Gly
             20                  25                  30

Asp Xaa Gly Gly Phe Gly
         35

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: PEPTIDE
<222> LOCATION: (4)..(12)
<223> OTHER INFORMATION: "Xaa" STANDS FOR A MONO- OR DIMETHYLATED ARGININE

<400> SEQUENCE: 14

Gly Asp Asp Xaa Xaa Gly Xaa Gly Gly Tyr Asp Xaa Gly Gly
 1               5                  10

<210> SEQ ID NO 15
<211> LENGTH: 26
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: PEPTIDE
<222> LOCATION: (4)..(22)
<223> OTHER INFORMATION: "Xaa" STANDS FOR A MONO- OR DIMETHYLATED ARGININE

<400> SEQUENCE: 15

Gly Gly Tyr Xaa Gly Xaa Gly Gly Asp Xaa Gly Gly Phe Xaa Gly Gly
1               5                   10                  15

Xaa Gly Gly Gly Asp Xaa Gly Gly Phe Gly
            20                  25

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic

<400> SEQUENCE: 16

Gly Arg Gly Arg Gly Arg Gly Arg Gly Arg Gly Arg Gly Arg Gly Arg
1               5                   10                  15

Gly Arg Gly

<210> SEQ ID NO 17
<211> LENGTH: 38
<212> TYPE: PRT
<213> ORGANISM: Artificial Sequence
<220> FEATURE:
<223> OTHER INFORMATION: Description of Artificial Sequence: Synthetic

<400> SEQUENCE: 17

Asp Val Glu Pro Lys Val Lys Ser Lys Lys Arg Glu Ala Val Ala Gly
1               5                   10                  15

Arg Gly Arg Gly Arg Gly Arg Gly Arg Gly Arg Gly Arg Gly Arg Gly
            20                  25                  30

Arg Gly Gly Pro Arg Arg
        35

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic

<400> SEQUENCE: 18

Ala Arg Gly Arg Gly Arg Gly Met Gly Arg Gly
1               5                   10

<210> SEQ ID NO 19
<211> LENGTH: 23
<212> TYPE: PRT
<213> ORGANISM: Artificial Sequence
<220> FEATURE:
<223> OTHER INFORMATION: Description of Artificial Sequence: Synthetic

<400> SEQUENCE: 19

Lys Ala Gln Val Ala Ala Arg Gly Arg Gly Arg Gly Met Gly Arg Gly
1               5                   10                  15

Asn Ile Phe Gln Lys Arg Arg
            20

<210> SEQ ID NO 20
<211> LENGTH: 46
<212> TYPE: PRT
<213> ORGANISM: Artificial Sequence
<220> FEATURE:
<223> OTHER INFORMATION: Description of Artificial Sequence: Synthetic

<400> SEQUENCE: 20

```
Gly Gly Gln Gln Asp Arg Gly Gly Arg Gly Arg Gly Gly Gly Gly
 1               5                  10                  15

Tyr Asn Arg Ser Ser Gly Gly Tyr Glu Pro Arg Gly Arg Gly Gly Gly
            20                  25                  30

Arg Gly Gly Arg Gly Gly Met Gly Gly Ser Asp Arg Gly Gly
            35                  40                  45
```

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: Synthetic

<400> SEQUENCE: 21

```
Gly Gly Gln Gln Asp Arg Gly Gly Arg Gly Arg Gly Gly Gly Gly
 1               5                  10                  15

Tyr Asn
```

<210> SEQ ID NO 22
<211> LENGTH: 26
<212> TYPE: PRT
<213> ORGANISM: Artificial Sequence
<220> FEATURE:
<223> OTHER INFORMATION: Description of Artificial Sequence: Synthetic

<400> SEQUENCE: 22

```
Ser Gly Gly Tyr Glu Pro Arg Gly Arg Gly Gly Arg Gly Gly Arg
 1               5                  10                  15

Gly Gly Met Gly Gly Ser Asp Arg Gly Gly
            20                  25
```

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic

<400> SEQUENCE: 23

```
Asp Phe Asn Arg Gly Gly Gly Asn Gly Arg Gly Gly Arg Gly Arg Gly
 1               5                  10                  15

Gly
```

<210> SEQ ID NO 24
<211> LENGTH: 29
<212> TYPE: PRT
<213> ORGANISM: Artificial Sequence
<220> FEATURE:
<223> OTHER INFORMATION: Description of Artificial Sequence: Synthetic

<400> SEQUENCE: 24

```
Asp Phe Asn Arg Gly Gly Gly Asn Gly Arg Gly Gly Arg Gly Arg Gly
 1               5                  10                  15

Gly Pro Met Gly Arg Gly Gly Tyr Gly Gly Gly Ser
            20                  25
```

<210> SEQ ID NO 25
<211> LENGTH: 38
<212> TYPE: PRT
<213> ORGANISM: Artificial Sequence
<220> FEATURE:
<223> OTHER INFORMATION: Description of Artificial Sequence: Synthetic

<400> SEQUENCE: 25

Gly Asp Asp Arg Arg Gly Arg Gly Gly Tyr Asp Arg Gly Tyr Arg
1               5                   10                  15

Gly Arg Gly Gly Asp Arg Gly Phe Arg Gly Arg Gly Gly Gly
            20                  25                  30

Asp Arg Gly Gly Phe Gly
            35

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 26

Gly Asp Asp Arg Arg Gly Arg Gly Gly Tyr Asp Arg Gly Gly
1               5                   10

<210> SEQ ID NO 27
<211> LENGTH: 26
<212> TYPE: PRT
<213> ORGANISM: Artificial Sequence
<220> FEATURE:
<223> OTHER INFORMATION: Description of Artificial Sequence: Synthetic

<400> SEQUENCE: 27

Gly Gly Tyr Arg Gly Arg Gly Gly Asp Arg Gly Gly Phe Arg Gly Gly
1               5                   10                  15

Arg Gly Gly Gly Asp Arg Gly Gly Phe Gly
            20                  25

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic

<400> SEQUENCE: 28

Asp Asn His Gly Arg Gly Arg Gly Arg Gly Arg Gly Arg Gly Gly
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 29

Gly Gly Arg Gly Arg Gly Gly Ser Gly Gly Arg Gly Arg Gly Gly
1               5                   10                  15

<210> SEQ ID NO 30
<211> LENGTH: 12
<212> TYPE: PRT
<213> ORGANISM: Artificial Sequence
<220> FEATURE:

-continued

<223> OTHER INFORMATION: Description of Artificial Sequence: Synthetic

<400> SEQUENCE: 30

Glu Arg Ala Arg Gly Arg Gly Arg Gly Arg Gly Glu
 1               5                  10

METHYLATED, SMD HOMOLOGOUS PEPTIDES, REACTIVE WITH THE ANTIBODIES FROM SERA OF LIVING BEINGS AFFECTED WITH SYSTEMIC LUPUS ERYTHEMATOSUS

The present invention relates to a method of producing certain peptides containing methylated arginines that are followed by a glycine residue and that constitute immunogenic determinants of antibodies present in sera from patients with systemic lupus erythematosus, or Epstein-Barr virus and wherein the methylation is a prerequisite for reacting with said antibodies. The invention also relates to the use of said peptides for diagnosis and treatment of systemic lupus erythematosus and related diseases, diseases in which Epstein-Barr virus has been implicated.

BACKGROUND OF THE INVENTION

Systemic lupus erythematosus is an autoimmune disease, in which the patient develops antibodies that react with many tissues of his own body. Dominant antibodies are directed against components of the cell nucleus, with epitopes that may be found in DNA, and in proteins that constitute small ribonucleoprotein particles (snRNPs).

The first laboratory test ever devised for this disease was the LE (lupus erythematosus) cell test. This test has to be repeated many times, before it results in a positive reaction in about 90% of the people with systemic lupus erythematosus. Also, the LE cell test is not specific for lupus, and can be positive in up to 20% of the people with rheumatoid arthritis, in some patients with other rheumatic conditions like Sjögren's syndrome or scleroderma, in patients with liver disease, and in persons taking drugs such as hydralazine and procainamide. The ANA test, which detects antibodies against nuclear antigens, is more specific for lupus than the LE test, and is positive in many patients that suffer from systemic lupus erythematosus. As with the LE test, a positive ANA is not diagnostic for lupus since the test may also be positive in people with scieroderma, dermatomyositis, rheumatoid arthritis, Sjögren's syndrome, in patients treated with certain drugs, or in patients suffering from infectious mononucleosis, liver disease, malaria etc. For these reasons and because the summed tests are expensive, new tests have been developed which are very helpful in the diagnosis of SLE. These include the anti-DNA antibody test, the anti-Sm antibody test, the anti-RNP antibody test, the anti-Ro antibody test, and tests which measure serum complement levels. Often, correct diagnosis will depend on the interpretation of many separate tests and symptoms.

The Sm antigen is a complex macromolecular structure consisting of 8 proteins (B, B', D1, D2, D3, E, F, G) associated with the U series of small RNA molecules. SmBB' and SmD are considered as the major antigenic components of the complex (for review see S. O. Hoch, 1989). However, SmBB' shows cross reactivity with the anti-RNP antibodies, consequently SmD is regarded as the most specific autoantigen for Sm (W. J. van Venrooij et al, 1991).

The SmD cDNA has been isolated from a human B-lymphocyte library with synthetic oligonucleotide probes, designed on the basis of the N-terminal sequence of SmD (Rokeach et al., 1988). Subsequently, it was shown that the in vitro transcription product could be immunoprecipitated by anti-Sm IgG. The D protein has since been characterized either as a doublet designated D and D' (Andersen et al., 1990) or as three polypeptides designated D1 (16 kDa), D2 (16.5 kDa) and D3 (18 kDa) (Lehmeier et al., 1990), D1 being identical with the SmD cloned by Rokeach et al. (1988). The sequence of D2 and D3 is substantially different from D1.

Over the years, several research groups have reported on the use of recombinant SmD and of SmD derived peptides and have published conflictory data. Rokeach et al. (1992a) expressed SmD1 in *E. coli* and in *S. cerivisiae*, but in contrast to the reactivity of natural SmD from HeLa cells, most of the patient anti-SmD sera bound recombinant SmD1 at a level not significantly higher than normal human sera. Nevertheless, the same group (Rokeach et al., 1992b) has performed epitope mapping based on multiple fusions between the TrpE gene and fragments of the SmD coding sequence, expressed in *E. coli*. Two patterns of anti-Sm reactivity emerged: discontinuous epitopes were found scattered over the full-length antigen, and a dominant epitope was located at the C-terminus, from amino acid 87 to 119 (Rokeach et al., 1992b). Using synthetic peptides, Barakat et al. (1990) showed that the N-terminus (peptide 1–20) and peptide 44–67 could be used as a valuable probe for SLE diagnosis although their results did not match the anti-SmD reactivity obtained by the traditional assay (patent EP-B-0491014). Using a similar strategy, Sabbatini et al. (1993a) have identified a dominant epitope in the C-terminal region of SmD1 (aa95–aa119) confirming the results of Rokeach et al. (1992b), but opposing the results obtained by Barakat et al. (1990). The most recent work on epitope mapping of SmD1 by means of synthetic peptides (James et al. 1994) showed that 8 of 9 SmD positive sera (precipitin positive) are reactive with the sequence spanning octapeptides 92–112. An additional epitope, clearly reactive with 7 of 9 SmD positive sera was located in the region of amino acid 82–90. Finally, a SmD-like epitope was recently identified by Rivkin et al. (1994) and consists of a (Gly-Arg)$_9$ dipeptide repeat (homology with the C-terminus). In contrast to the SLE specificity of anti-Sm antibodies, the defined epitope is also recognized by patients with other autoimmune diseases (rheumatoid arthritis, scleroderma, Sjögren's syndrome). The βgalactosidase fusion protein in *E. coli* of the above mentioned epitope was reactive with 35% of the SLE sera, but only 6 out of these 32 positive sera were reactive with the native SmD protein indicating that the fusion protein is less specific than the native SmD protein. Vice versa, only four of eight SmD sera reacted with the fusion protein. It should be noted however, that SmD was also expressed as a full-size β-galactosidase fusion protein in *E. coli* (Wagatsuma et al. 1993), but that this recombinant SmD antigen was not recognized by patient sera, although all sera recognized the natural Sm 16 kDa antigen on Western blot.

In conclusion, none of the described synthetic peptides nor the entire recombinant protein or parts of the molecule result in an immunoreactivity identical with the reactivity obtained with natural SmD.

SUMMARY OF THE INVENTION

It is an aim of the present invention to provide peptides which have a high reactivity for antibodies present in sera from patients with systemic lupus erythematosus.

Another aim of the present invention is to provide methods for obtaining said peptides.

Another aim of the present invention is to provide methods of raising antibodies specifically reactive with peptides of said peptides, thereby mimicking said peptides.

Another aim of the present invention is to provide methods of raising anti-idiotype antibodies specifically reactive with the afore mentioned antibodies.

Another aim of the present invention is to provide a pharmaceutical composition consisting of these peptides, for therapy or diagnosis.

Another aim of the present invention is to provide a diagnostic kit for systemic lupus erythematosus.

All these aims of the present invention are met by the following embodiments of the present invention.

According to its main embodiment the present invention relates to peptides containing less than 50 amino acids, comprising at least one dimer of the type XG, wherein X stands for a methylated arginine residue, and that are able to react with antibodies, with said methylation being crucial for the reaction between said peptide and said antibodies, and wherein said antibodies are present in sera from patients with systemic lupus erythematosus, or infectious, recurrent or chronic mononucleosis, or certain cancers which are related to infection with Epstein-Barr virus, such as Burkitt's lymphoma or nasopharyngeal carcinoma.

According to a further embodiment the present invention also relates to a peptide and/or chemical structure comprising any of the above mentioned peptides, fused to a linker molecule. The present invention also relates to peptides comprising and/or consisting of tandem repeats of at least two of any of the above mentioned peptides, or branched peptides that comprises at least one of the above mentioned peptides.

According to a more specific embodiment the present invention also relates to a method for producing any of the above mentioned peptides, by classical chemical synthesis, wherein methylated arginines are substituted for unmethylated arginine residues at certain steps during the chemical synthesis. The present invention also relates to a method for producing any of the above mentioned peptides, wherein the primary amino acid sequence is produced by classical chemical synthesis, and wherein the arginine residues that precede glycine residues are subsequently methylated by contacting said peptides with a protein arginine methyltransferase. The present invention also relates to a method for producing any of the above mentioned peptides comprising the following steps: (i) transforming an appropriate cellular host with a recombinant vector in which a polynucleic acid is inserted comprising the sequence that codes for said peptide under the control of the appropriate regulatory elements such that said peptide or a protein comprising said peptide is expressed and/or secreted, (ii) culturing said transformed cellular host under conditions allowing expression of said protein or peptide and allowing a partial or optimal methylation of the arginines present in said peptide, and (iii) harvesting said peptide. The present invention also relates to a method for producing any of the above mentioned peptides comprising the following steps: (i) transforming an appropriate cellular host with a recombinant vector in which a polynucleic acid is inserted comprising the sequence that codes for said peptide under the control of the appropriate regulatory elements, such that said peptide or a protein comprising said peptide is expressed and/or secreted, (ii) culturing said transformed cellular host under conditions allowing expression of said protein or said peptide, (iii) harvesting said protein or said peptide, and (iv) methylating arginine residues of said protein or said peptide by contacting with a protein arginine methyltransferase. According to a more specific embodiment the present invention also relates to any of the above mentioned methods, wherein said host cell is a bacterial host or yeast or any other eukaryotic host cell which is preferably transformed with a recombinant baculovirus.

According to a preferred embodiment the present invention also relates to an antibody raised upon immunization with any of the above mentioned peptides, with said antibody being specifically reactive with the methylated forms of said peptide, and with said antibody being preferably a monoclonal antibody. The present invention also relates to an anti-idiotype antibody raised upon immunization with any antibody as defined above, with said anti-idiotype antibody being specifically reactive with said antibody, thereby mimicking the methylated form of any above mentioned peptide, and with said antibody being preferably a monoclonal antibody.

According to a more specific embodiment the present invention also relates to an immunotoxin molecule comprising and/or consisting of a cell recognition molecule being a peptide as defined above, or an antibody as defined above, covalently bound to a toxin molecule or active fragment thereof.

According to a further embodiment the present invention relates to any of the above mentioned peptides or antibodies or immunotoxine molecules or a composition thereof for use as a medicament. Said use can have the purpose of a medicament for treatment or of a diagnosticum for any of the following auto-immune diseases: systemic lupus erythematosus, discoid lupus erythematosus, scleroderma, dermatomyositis, rheumatoid arthritis, Sjögren's syndrome, or for diseases in which Epstein-Barr virus can be implicated such as Burkitt's lymphoma or nasopharyngeal carcinoma, or infectious, recurrent or chronic mononucleosis. More specifically, the present invention relates to a treatment for auto-immune diseases by increasing the size of antigen-immune complexes, thereby improving the clearance of the formed immune complexes. The present invention also relates to a treatment for auto-immune diseases by inducing a state of systemic hyporesponsiveness to the auto-antigen after oral administration of any of the above mentioned peptides or antibodies or immunotoxine molecules or a composition thereof, thereby preventing the pathogenic production of anti-self antibodies like anti-Sm antibodies or anti-DNA antibodies. The present invention also relates to a diagnostic kit for use in detecting any of the afore mentioned diseases, wherein said kit comprises at least one of the above mentioned peptides or antibodies, and with said peptide or antibody being possibly bound to a solid support. More preferably said kit is comprising a range of said peptides or said antibodies, possibly in combination with native methylated SmD1 or SmD3 or Sm69 and recombinant unmethylated SmD1 or SmD3 or Sm69, wherein said peptides are attached to specific locations on a solid substrate. More preferably said solid support is a membrane strip and said polypeptides are coupled to the membrane in the form of parallel lines. It has to be understood that certain peptides, or antibodies as defined above, alternatively, are not attached to a solid support but are provided in the binding solution to be used as competitors and/or to block other antibodies that are present in sera from patients with autoimmune diseases other than SLE, thereby decreasing or eliminating possible cross-reaction and/or aspecific binding.

DETAILED DESCRIPTION OF PREFERRED EMBODIMENTS

Figure 1:
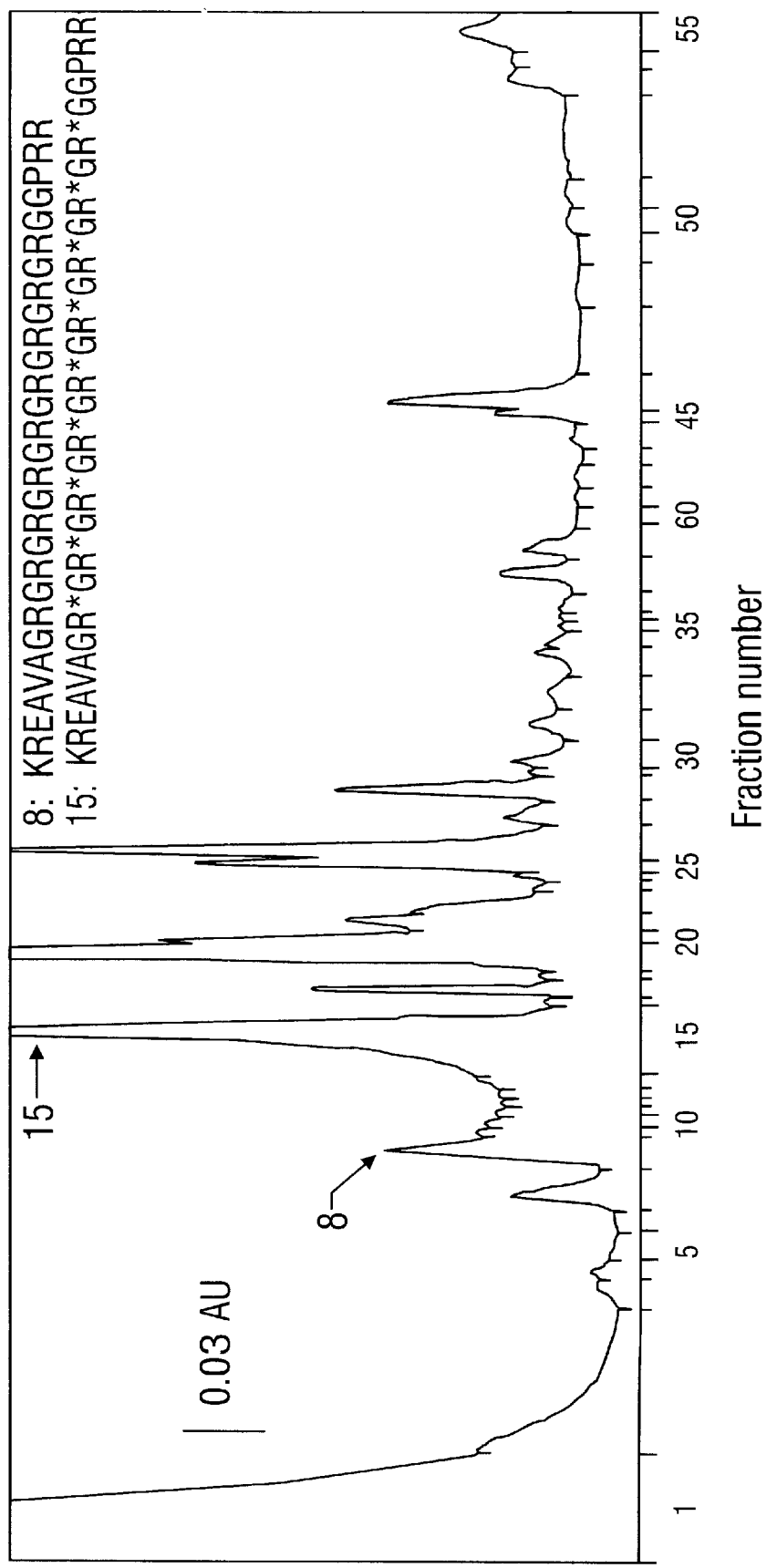
FIG. 1: HPLC profile of the Endo-Lys digest.

We have demonstrated for the first time that well defined secondary modifications (mostly $N^G,N^G$-dimethylarginine) are present on the Arg residues of the C-terminal peptide, that are followed by a glycine residue. Moreover, we have raised evidence that the C-terminal peptide can only show an immunoreactivity almost identical to the immunoreactivity of natural SmD, if these arginine residues are methylated. These dimethylarginines present on the nine Arg positions of the C-terminus, have been demonstrated for the first time in the natural SmD1 molecule. In SmD2 no dimethylarginine was retrieved while in the C-terminus of SmD3 the four RG motifs in the C-terminus again were found to be dimethylated.

The amino acid $N^G,N^G$-dimethylarginine is the result of a post-translational modification which seems to occur predominantly in RNA binding proteins (Najbauer, 1993). These nuclear proteins are enzymatically modified by a nuclear protein methylase I ( S-adenosyl-methionine: protein-arginine N-methyltransferase, E.C.2.1.1.23; Rajpurohit, et al., 1994). The structural specificity of this enzyme seems to be an arginine containing peptide with glycine in the C-flanking position as was shown by substrate evaluation with synthetic peptides (Rawal, 1995). Nevertheless, in the same study it was demonstrated that the entire molecule also plays an important though thus far unknown role in the methylation process. Interestingly, this cellular methylation process can be mimicked in vitro with purified methylaseI as was illustrated with recombinant heterogeneous nuclear RNP protein A1 (Rajpurohit, et al. 1994)

From our results, we thus can conclude that in SmD immunoreactivity, at least 2 epitopes are involved. One of the epitopes is apparently present in the recombinant SmD1 molecule and can not be assigned to a linear epitope (epitope mapping of E. coli recombinant SmD1, data not shown). This is in agreement with the discontinuous epitope described by Rokeach et al. (1992b). The epitope localized at the C-terminus both by epitope mapping with E. coli fusion fragments (Rokeach et al., 1992b; Rivkin et al., 1994) and synthetic peptides (Sabbatini et al., 1993a; James et al., 1994) could well be explained by the work of Rivkin et al. (1994). The latter group has demonstrated that a dipeptide repeat $(Gly-Arg)_9$ is recognized by 35% of sera from SLE patients but also by 15% of sera from other autoimmune diseases. This result is in contrast with the high SLE specificity of the anti-Sm antibodies. Indeed, the specificity of the unmodified C-terminal SmD1 peptide has not been thoroughly investigated by Rokeach (1992b) nor by James et al. (1994). Only Sabbatini (1993a) described a certain disease specificity for the C-terminal synthetic peptide. On one hand, Rivkin has shown that out of 32 sera positive for the $(Gly-Arg)_9$ peptide, only 6 sera are positive with native SmD. On the other hand, of the positive SmD sera identified on Western blot, only half of them are reactive with the unmodified C-terminal peptide (Rivkin: 4/8; Rokeach 9/19; Sabbatini: 5/9). Based on these results it can be concluded that immunoreactivity of the unmodified C-terminal peptide does not well correlate with natural SmD and is less SLE specific than natural SmD. In contrast, our results show that 15 out of 17 SmD positive sera are immunoreactive with the dimethylated C-terminal peptide while only one serum reacts with the unmodified C-terminal peptide. The 2 sera that do not recognize the dimethylated C-terminal peptide are immunoreactive with the total recombinant SmD and are apparently monospecific for the discontinuous epitope.

In conclusion, natural SmD1 contains nine dimethylated arginines at the C-terminus and this modification plays a crucial role in the SLE specific immunoreactivity of the SmD antigen.

According to its main embodiment the present invention relates to peptides that contain arginine residues that are immediately followed by a glycine residue, and wherein at least one arginine residue is methylated or dimethylated at one terminal aminogroup of the guanidino-group of the arginine residue, and wherein this methylation is a prerequisite for the peptide to be recognized by antibodies that characterize certain diseases. Antibodies that are specifically reacting with this type of peptides can be found in sera from patients with systemic lupus erythematosus or related autoimmune diseases such as discoid lupus erythematosus, or patients with infectious mononucleosis, or recurrent or chronic mononucleosis, or that suffer from diseases in which Epstein-Barr virus has been implicated such as nasopharyngeal carcinoma and Burkitt's lymphoma.

Peptides are described which immunologically mimic the immunogenic determinants of self proteins recognized by the immune system in patients suffering from lupus erythematosus. A crucial aspect of such peptides is the fact that arginines followed by a glycine are methylated. One peptide (SmD1) has been demonstrated to contain a stretch of 9 consecutive arginine-glycine residues, wherein each arginine is methylated and wherein this methylation is necessary for specific recognition by antibodies present in sera of patients with lupus erythematosus. A second peptide (SmD3) has been demonstrated to contain isolated arginine-glycine residues, wherein the arginine is methylated. Also, a third peptide (Sm69) has been demonstrated to contain several domains characterised by several arginine-glycine residues, wherein the arginine is dimethylated. It is therefore anticipated that the presence of one dimethylated arginine, followed by a glycine can be sufficient for specific recognition by some antibodies present in sera of patients with lupus erythematosus. The invention therefore relates to those peptides wherein at least one arginine residue is followed by a glycine, wherein the arginine residue is methylated, and wherein this methylation is necessary for specific recognition by antibodies.

The term 'peptide' as used throughout the specification and claims refers to a polymer of amino acids and does not refer to a specific length of the product; thus, oligopeptides, polypeptides and proteins are included within the definition of 'peptide'. This term also does not refer to or exclude post-expression modifications of the peptide, for example, glycosylations, acetylations, phosphorylations and the like. Included within the definition are, for example, peptides containing one or more analogues of an amino acid (including, for example, unnatural amino acids, PNA, etc.), polypeptides with substituted linkages, as well as other modifications known in the art, both naturally occurring and non-naturally occurring.

Whenever the expression "peptide containing less than 50 amino acids" is used, this should be interpreted in a broad sense, as a means of circumscribing an essentially truncated version of entire immunoreactive proteins that still comprises the highly reactive domain characterized by the presence of methylated arginine residues. These peptides have a length of preferably 40, 30, 25, 20 or less amino acids. The present invention also relates to peptides having a length of 50, 60 or more amino acids without comprising the full length of the native protein. It is for practical purpose of peptide synthesis that peptides containing less than 50 amino acids are defined.

With 'immunogenic determinant' is meant, those chemical groupings comprising a primary amino acid sequence, and secondary modifications of the amino acid residues in a certain three-dimensional arrangement, that together determine the specific reactivity of the entire antigen for a raised antibody. Such antibody can also recognize different chemical groupings, which are then termed to 'immunologically mimic' the immunogenic determinant.

When secondary modifications of a peptide are said to be 'necessary' or 'crucial', or to 'be a prerequisite' for reacting with an antibody, the absence of said secondary modifications will result in a peptide of which the dissociation constant for interaction with said antibody will be at least two orders of magnitude higher than the dissociation constant for the interaction between said antibody and the peptide wherein the secondary modifications are present, preferably three orders of magnitude higher, and more preferably four orders of magnitude higher.

The term 'crossreaction' refers to the reaction of one antigen with antibodies developed against another antigen or antibodies that are found in sera from patients with different diseases.

The term 'methylated arginine' as used throughout the ensuing specification and claims is used in a broad sense and refers any methylated form. More preferably the term methylated refers to a dimethylated form of arginine in which one amino-group of the guanidino group of the arginine residue is substituted with one or two methyl groups. The term 'methylation' refers to the process that results in said forms of arginine.

It has to be understood that the peptides of the present invention are not limited to include only those peptides that are recognized by antibodies specific for systemic lupus erythematosus, but also relate to those peptides that react with antibodies associated with related autoimmune diseases such as discoid lupus erythematosus and scleroderma or peptides that are related to infection with Epstein-Barr virus such as infectious, recurrent, or chronic mononucleosis. Several autoimmune diseases are related to systemic lupus erythematosus such as discoid lupus erythematosus, scleroderma. The antibodies that are present in sera of patients with these autoimmune diseases tend to recognize self-antigens, that are often localized in the nucleus and present in all tissues. As a result, similar or analogous epitopes are often recognized, thereby leading to crossreactivity, and difficult diagnosis.

The few antibodies present in sera from patients with systemic lupus erythematosus that are also able to react with recombinant and thus unmethylated C-terminal parts of SmD1, were shown to cross-react with the EBNA-1 Epstein-Barr virus associated nuclear antigen, of which the primary sequence displays homology with the primary sequence of SmD1 (Sabbatini et al., 1993b). EBNA-1 is the only protein which is consistently expressed during latency of Epstein-Barr virus. The extreme persistence of Epstein-Barr virus during latency can be explained by the very low immunogenicity of this viral protein. EBNA-1 most importantly contains six arginine residues which are followed by a glycine. It can therefore be anticipated that the frequency of finding specific antibodies in sera from patients with mononucleosis (infected with Epstein-Barr virus) or from people with recurrent, or chronic mononucleosis or with a history of mononucleosis, will increase, when antigens (such as EBNA-1) are used wherein the arginine residues that precede a glycine residue are methylated, as we have shown to be the case with the antibodies directed against SmD-1 in patients with lupus erythematosus.

According to a more specific embodiment the present invention relates to those peptides that contain methylated arginine residues that are preceding glycine residues, wherein said methylation is crucial for high-affinity interaction with antibodies that are found in sera from patients with autoimmune diseases such as systemic lupus erythematosus, or that are infected with Epstein Barr virus.

The present invention also relates to those peptides wherein the arginine-glycine doublets are repeated, at least once, and more preferably 3 or 4 or 5 or 6 or 7 or 8 times, and even more preferably 9 times, as is the case with the natural antinuclear antigen SmD-1, and wherein at least one arginine residue that precedes a glycine residue is methylated, preferably dimethylated, with said methylation being necessary for specific reaction with antibodies, for instance with antibodies found in sera from patients with SLE.

In a more specific embodiment, the present invention relates to a peptide that is characterized by the amino acid sequence Gly Arg Gly Arg Gly Arg Gly Arg Gly Arg Gly Arg Gly Arg Gly Arg Gly Arg Gly. (SEQ ID NO 16) wherein at least one and preferably each arginine is methylated, preferably dimethylated and even more preferably dimethylated in an asymmetric way, thereby mimicking the main immunogenic determinant of the C-terminal part of antinuclear antigen SmD1.

In a more specific embodiment, the present invention relates to a peptide that is characterized by the amino acid sequence Asp Val Glu Pro Lys Val Lys Ser Lys Lys Arg Glu Ala Val Ala Gly Arg Gly Arg Gly Arg Gly Arg Gly Arg Gly Arg Gly Arg Gly Arg Gly Arg Gly Gly Pro Arg Arg. (SEQ ID NO 17) wherein at least one and preferably each arginine that precedes a glycine, is methylated, preferably dimethylated and even more preferably dimethylated in an asymmetric way, thereby mimicking the main immunogenic determinant of the C-terminal part of antinuclear antigen SmD1.

In a more specific embodiment, the present invention relates to a peptide that is characterized by the amino acid sequence Ala Arg Gly Arg Gly Arg Gly Met Gly Arg Gly.

(SEQ ID NO 18) wherein at least one and preferably each arginine is methylated, preferably dimethylated and even more preferably dimethylated in an asymmetric way, thereby mimicking the main immunogenic determinant of the C-terminal part of antinuclear antigen SmD3.

In a more specific embodiment, the present invention also relates to a peptide that is characterized by the amino acid sequence Lys Ala Gln Val Ala Ala Arg Gly Arg Gly Arg Gly Met Gly Arg Gly Asn Ile Phe Gln Lys Arg Arg. (SEQ ID NO 19) wherein at least one and preferably each arginine that precedes a glycine is methylated, preferably dimethylated and even more prefeably dimethylated in an asymmetric way, thereby mimicking the main immunogenic determinant and its borders of the C-terminal part of antinuclear antigen SmD3.

According to a more specific embodiment, the present invention also relates to a peptide that comprises or consists of by the amino acid sequence Gly Gly Gln Gln Asp Arg Gly Gly Arg Gly Arg Gly Gly Gly Gly Gly Tyr Asn Arg Ser Ser Gly Gly Tyr Glu Pro Arg Gly Arg Gly Gly Gly Arg Gly Gly Arg Gly Gly Met Gly Gly Ser Asp Arg Gly Gly. (SEQ ID NO 20) or Gly Gly Gln Gln Asp Arg Gly Gly Arg Gly Arg Gly Gly Gly Gly Gly Tyr Asn. (SEQ ID NO 21) or Ser Gly Gly Tyr Glu Pro Arg Gly Arg Gly Gly Gly Arg Gly Gly Arg Gly Gly Met Gly Gly Ser Asp Arg Gly Gly. (SEQ ID NO 22) or Asp Phe Asn Arg Gly Gly Gly Asn Gly Arg Gly Gly Arg Gly Arg Gly Gly. (SEQ ID NO 23) or Asp Phe Asn Arg Gly Gly Asn Gly Arg Gly Gly Arg Gly Arg Gly Gly Pro Met Gly Arg Gly Gly Tyr Gly Gly Gly Gly Ser. (SEQ ID NO 24) or Gly Asp Asp Arg Arg Gly Arg Gly Gly Tyr Asp Arg Gly Gly Tyr Arg Gly Arg Gly Gly Asp Arg Gly Gly Phe Arg Gly Gly Arg Gly Gly Gly Asp Arg Gly Gly Phe Gly. (SEQ ID NO 25) or Gly Asp Asp Arg Arg Gly Arg Gly Gly Tyr Asp Arg Gly Gly. (SEQ ID NO 26) or Gly Gly Tyr Arg Gly Arg Gly Gly Asp Arg Gly Gly Phe Arg Gly Gly Arg Gly Gly Gly Asp Arg Gly Gly Phe Gly. (SEQ ID NO 27) wherein at least one and preferably each arginine that precedes a glycine is methylated, preferably dimethylated and even more preferably dimethylated in an asymmetric way, thereby mimicking the main immunogenic determinant and its borders of the C-terminal part of antinuclear antigen Sm69.

According to a more specific embodiment, the present invention relates to a peptide that comprises or consists of the amino acid sequence Asp Asn His Gly Arg Gly Arg Gly Arg Gly Arg Gly Arg Gly Gly Gly. (SEQ ID NO 28) or Gly Gly Arg Gly Arg Gly Gly Ser Gly Gly Arg Gly Arg Gly Gly. (SEQ ID NO 29) or Glu Arg Ala Arg Gly Arg Gly Arg Gly Arg Gly Glu. (SEQ ID NO 30) wherein at least one and preferably each arginine that precedes a glycine is methylated, preferably dimethylated and even more preferably dimethylated in an asymmetric way, thereby mimicking the Epstein-Barr virus nuclear antigen1.

The present invention also relates to molecular structures in which at least part represents a peptide or antibody as defined above. Such molecular structures can result from fusion of peptides of the present invention with peptides and/or proteins and/or other molecules that are further characterized in that they specifically interact with other peptides and/or proteins and/or molecular structures, enabling tagging and/or binding of the fused polypeptide and/or protein to specific tissue- or cell types or that allow for purification of said molecular structures due to the presence of for instance 4, or 5 or 6 consecutive histidine residues, or are cytotoxic to T-cells and/or B-cells such as cholera toxin, or allow for labelling by means of a radioactive or fluorescent or immunogold or enzymatic marker.

It may also be desirable in certain instances to join two or more peptides together in one peptide structure, or to create branched peptides. One advantage of this arrangement is well known in the art and relates to diagnosis. When antibodies are used in an assay in order to detect the present antigens, tandem repeats or branched peptides of the antigens can increase the amount of immobilized antigens -presented to the antibodies and thereby increase the sensitivity of the assay. The sensitivity can be increased exponentially when the immobilized antigens are used together with a specific concentration of such antigens in a soluble form, thereby inducing the formation of crosslinked antigen-immunoprecipitates. A second advantage relates to therapy. The deposition of self-antigen autoimmune complexes in various tissues is an important step towards the acquisition of a pathological condition. It is generally accepted that the main cause of said deposition is the insufficient blood clearance by the liver of the antigen-immune complexes due to the small size of said complexes. Administration of tandem repeats or branched forms of said peptides could increase the size of the formed antigen-immune complexes, and thereby increase the clearance and thus decrease the deposition of said complexes.

The present invention also relates to circularized forms of said peptides, the advantage being well known in the art, and relating to an increased affinity of a conformationally constraint peptide as compared with the more randomly coiled forms of linear peptides.

In order to accommodate for eventual negative characteristics of the claimed peptides, such as rapid degradation, solubility, cytotoxic effects and so on, the skilled person will be able to design conservative as well as non-conservative amino acid substitutions, or substitutions with non-natural amino acids, PNA etc. These will generally account for less than 35 percent of a specific sequence. Such peptides also include peptides with substituted linkages, as well as other modifications known in the art, both naturally occurring and non-naturally occurring. It may be desirable in cases where the SmD peptides or other antigenic peptides of the present invention are highly polymorphic, to vary one or more of the amino acids so as to better mimic the different epitopes of several viral strains, or as recognized by antibodies in sera from patients with SLE or other autoimmune diseases.

The present invention also relates to any analogs of the peptides of the present invention.

The term "analog" as used throughout the specification or claims to describe the proteins or peptides of the present invention, includes any protein or peptide having an amino acid residue sequence substantially identical to a sequence specifically shown herein in which one or more residues have been conservatively substituted with a biologically equivalent residue. Examples of conservative substitutions include the substitution of hydrophobic residue such as isoleucine, valine, leucine or methionine for another, the substitution of one hydrophilic residue for another such as between arginine and lysine, between glutamine and asparagines, between glycine and serine, the substitution of one basic residue such as lysine, arginine or histidine for another, or the substitution of one acidic residue, such as aspartic acid or glutamic acid for another. Examples of allowable mutations according to the present invention can be found in Table 4.

TABLE 4

Overview of the amino acid substitutions which could form the basis of analogs (muteins) as defined above

| Amino acids | Synonymous groups |
|---|---|
| Ser (S) | Ser, Thr, Gly, Asn |
| Arg (R) | Arg, His, Lys, Glu, Gln |
| Leu (L) | Leu; Ile, Met, Phe, Val, Tyr |
| Pro (P) | Pro, Ala, Thr, Gly |
| Thr (T) | Thr, Pro, Ser, Ala, Gly, His, Gln |
| Ala (A) | Ala, Pro, Gly, Thr |
| Val (V) | Val, Met, Ile, Tyr, Phe, Leu, Val |
| Gly (G) | Gly, Ala, Thr, Pro, Ser |
| Ile (I) | Ile, Met, Leu, Phe, Val, Ile, Tyr |
| Phe (F) | Phe, Met, Tyr, Ile, Leu, Trp, Val |
| Tyr (Y) | Tyr, Phe, Trp, Met, Ile, Val, Leu |
| Cys (C) | Cys, Ser, Thr, Met |
| His (H) | His, Gln, Arg, Lys, Glu, Thr |
| Gln (Q) | Gln, Glu, His, Lys, Asn, Thr, Arg |
| Asn (N) | Asn, Asp, Ser, Gln |
| Lys (K) | Lys, Arg, Glu, Gln, His |
| Asp (D) | Asp, Asn, Glu, Gln |
| Glu (E) | Glu, Gln, Asp, Lys, Asn, His, Arg |
| Met (M) | Met, Ile, Leu, Phe, Val |

The phrase "conservative substitution" also includes the use of a chemically derivatized residue in place of a non-derivatized residue provided that the resulting protein or peptide is biologically equivalent to the protein or peptide of the invention.

"Chemical derivative" refers to a protein or peptide having one or more residues chemically derivatized by reaction of a functional side group or peptides with substituted linkages, as well as other modifications known in the art, both naturally occurring and non-naturally occurring. Examples of such derivatized molecules, include but are not limited to, those molecules in which free amino groups have been derivatized to form amine hydrochlorides, p-toluene sulfonyl groups, carbobenzoxy groups, t-butyloxycarbonyl groups, chloracetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those proteins or peptides which contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. The peptides of the present invention also include any protein or peptide having one or more additions and/or deletions or residues relative to the sequence of a peptide whose sequence is shown herein, as long as the peptide is biologically equivalent to the proteins or peptides of the invention.

Furthermore, additional amino acids or chemical groups may be added to the amino- or carboxyl terminus for the purpose of creating a "linker arm" by which the peptide can conveniently be attached to a carrier. The linker arm will be at least one amino acid and may be as many as 60 amino acids but will most frequently be 1 to 10 amino acids. The nature of the attachment to a solid phase or carrier can be non-covalent as well as covalent. Possible arrangements of this nature are well described in the art. Natural amino acids such as histidine, cysteine, lysine, tyrosine, glutamic acid, or aspartic acid may be added to either the amino- or carboxyl terminus to provide functional groups for coupling to a solid phase or a carrier. However' other chemical groups such as, for example, biotin and thioglycolic acid, may be added to the termini which will endow the peptides with desired chemical or physical properties. The termini of the peptides may also be modified, for example, by N-terminal acetylation or terminal carboxy-amidation. In each instance, the peptide will preferably be as small as possible while still maintaining substantially all of the sensitivity of the larger peptide.

The peptides of the invention, and particularly the fragments, can be prepared by classical chemical synthesis. The synthesis can be carried out in homogeneous solution or in solid phase. For instance, the synthesis technique in homogeneous solution which can be used is the one described by Houbenweyl in the book entitled "Methode der organischen chemie" (Method of organic chemistry) edited by E. Wunsh, vol. 15-I et II. THIEME, Stuttgart 1974. The polypeptides of the invention can also be prepared in solid phase according to the methods described by Atherton and Shepard in their book entitled "Solid phase peptide synthesis" (IRL Press, Oxford, 1989). The methylated forms of the claimed peptides can be obtained by substituting the methylated arginine derivatives for the normal arginine derivatives during the classical chemical synthesis, or by contacting the unmethylated peptides after synthesis with a protein arginine methyl transferase enzyme of any eukaryotic origin.

The polypeptides according to this invention can also be prepared by means of recombinant DNA techniques as described, by Maniatis et al., Molecular Cloning: A Laboratory Manual, New York, Cold Spring Harbor Laboratory, 1982) by insertion of a polynucleic acid sequence encoding the claimed peptides or part of the claimed peptides in an appropriate vector and transforming a suitable host with said vector. This recombinant expression vector comprises a polynucleic acid or a part thereof as defined above, operably linked to prokaryotic, eukaryotic or viral transcription and translation control elements. In addition this sequence can be operably linked with sequences that allow for secretion of the claimed peptides. The term 'vector' may comprise a plasmid, a cosmid, a phage or a virus or a transgenic organism. Particularly useful may be BCG or adenoviral vectors, as well as avipox recombinant viruses.

The recombinant peptides can be methylated in vitro, by contacting the expressed and/or secreted peptides with a protein arginine methyl transferase of any eukaryotic origin, or in vivo by choosing the appropriate host, like yeast, or any eukaryotic cell, and more preferably by using the baculovirus transformation system.

The present invention does not exclude the option of using additional proteins like the BTG1 and TIS21 proteins which have been demonstrated to be essential for methylation in vivo (as a co-expressed protein) or to be required for optimal methylation in vitro (Lin et al., 1996), or any other proteins, peptides or chemical substances that can optimize the level of methylation.

Also any of the known purification methods for recombinant peptides can be used for the production of the recombinant peptides of the present invention.

The present invention also relates to a recombinant expression vector comprising a polynucleic acid or a part thereof as defined above, operably linked to prokaryotic, eukaryotic or viral transcription and translation control elements.

In general, said recombinant vector will comprise a vector sequence, an appropriate prokaryotic, eukaryotic or viral promoter sequence followed by a nucleotide sequence encoding a peptide as defined above, with said recombinant vector allowing the expression and/or secretion of any one of the polypeptides as defined above in a prokaryotic, or eukaryotic host or in living mammals when injected as naked DNA.

Also any of the known purification methods for recombinant proteins may be used for the production of the recombinant polypeptides of the present invention.

The term "vector" may comprise a plasmid, a cosmid, a phage, or a virus or a transgenic animal. Particularly useful for vaccine development may be BCG or adenoviral vectors, as well as avipox recombinant viruses.

The present invention also relates to a method for the production of a recombinant polypeptide as defined above, comprising:

transformation of an appropriate cellular host with a recombinant vector, in which a polynucleic acid or a part thereof according to as defined above has been inserted under the control of appropriate regulatory elements, culturing said transformed cellular host under conditions enabling the expression and/or secretion of said insert, and, harvesting said polypeptide.

The term "recombinantly expressed" used within the context of the present invention refers to the fact that the proteins of the present invention are produced by recombinant expression methods be it in prokaryotes, or lower or higher eukaryotes as discussed in detail below.

The term "lower eukaryote" refers to host cells such as yeast, fungi and the like. Lower eukaryotes are generally (but not necessarily) unicellular. Preferred lower eukaryotes are yeasts, particularly species within *Saccharomyces, Schizosaccharomyces, Kluveromyces, Pichia* (e.g. *Pichia pastoris*), *Hansenula* (e.g. *Hansenula polymorpha*), *Yarowia, Schwaniomyces, Schizosaccharomyces, Zygosaccharomyces* and the like. *Saccharomyces cerevisiae, S. carlsbergensis* and *K. lactis* are the most commonly used yeast hosts, and are convenient fungal hosts.

The term "prokaryotes" refers to hosts such as *E. coli, Lactobacillus, Lactococcus, Salmonella, Streptococcus, Bacillus subtilis* or *Streptomyces*. Also these hosts are contemplated within the present invention.

The term "higher eukaryote" refers to host cells derived from higher animals, such as mammals, reptiles, insects, and the like. Presently preferred higher eukaryote host cells are derived from Chinese hamster (e.g. CHO), monkey (e.g. COS and Vero cells), baby hamster kidney (BHK), pig kidney (PK15), rabbit kidney 13 cells (RK13), the human osteosarcoma cell line 143 B, the human cell line HeLa and human hepatoma cell lines like Hep G2, and insect cell lines (e.g. *Spodoptera frugiperda*). The host cells may be provided in suspension or flask cultures, tissue cultures, organ cultures and the like. Alternatively the host cells may also be transgenic animals.

The term "recombinant polynucleotide" or "nucleic acid" intends a polynucleotide or nucleic acid of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term "recombinant host cells", "host cells", "cells", "cell lines", "cell cultures", and other such terms denoting microorganisms or higher eukaryotic cell lines cultured as unicellular entities refer to cells which can be or have been, used as recipients for a recombinant vector or other transfer polynucleotide, and include the progeny of the original cell which has been transfected. It is understood that the progeny of a single parental cell may not necessarily be completely identical in morphology or in genomic or total DNA complement as the original parent, due to natural, accidental, or deliberate mutation.

The term "replicon" is any genetic element, e.g., a plasmid, a chromosome, a virus, a cosmid, etc., that behaves as an autonomous unit of polynucleotide replication within a cell; i.e., capable of replication under its own control.

The term "vector" is a replicon further comprising sequences providing replication and/or expression of a desired open reading frame.

The term "control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, splicing sites and terminators; in eukaryotes, generally, such control sequences include promoters, splicing sites, terminators and, in some instances, enhancers. The term "control sequences" is intended to include, at a minimum, all components whose presence is necessary for expression, and may also include additional components whose presence is advantageous, for example, leader sequences which govern secretion.

The term "promoter" is a nucleotide sequence which is comprised of consensus sequences which allow the binding of RNA polymerase to the DNA template in a manner such that mRNA production initiates at the normal transcription initiation site for the adjacent structural gene.

The expression "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

The polynucleic acids encoding the peptides of the present invention and inserted into the vector sequence may be attached to a signal sequence. Said signal sequence may be that from any source, e.g. the IgG or tissue plasminogen activator (tpa) leader sequence for expression in mammalian cells, or the a-mating factor sequence for expression into yeast cells.

A variety of vectors may be used to obtain the peptides of the present invention. Lower eukaryotes such as yeasts and glycosylation mutant strains are typically transformed with plasmids, or are transformed with a recombinant virus. The vectors may replicate within the host independently, or may integrate into the host cell genome.

Higher eukaryotes may be transformed with vectors, or may be infected with a recombinant virus, for example a recombinant vaccinia virus. Techniques and vectors for the insertion of foreign DNA into vaccinia virus are well known in the art, and utilize, for example homologous recombination. A wide variety of viral promoter sequences, possibly terminator sequences and poly(A)-addition sequences, possibly enhancer sequences and possibly amplification sequences, all required for the mammalian expression, are available in the art. Vaccinia is particularly preferred since vaccinia halts the expression of host cell proteins. Vaccinia is also very much preferred since it allows the expression of f.i. peptides of the present invention in cells or individuals which are immunized with the live recombinant vaccinia virus. For vaccination of humans the avipox and Ankara Modified Virus (AMV) are particularly useful vectors.

Also known are insect expression transfer vectors derived from baculovirus *Autographa californica* nuclear polyhedrosis virus (AcNPV), which is a helper-independent viral expression vector. Expression vectors derived from this system usually use the strong viral polyhedrin gene promoter to drive the expression of heterologous genes. Different vectors as well as methods for the introduction of heterologous DNA into the desired site of baculovirus are available to the man skilled in the art for baculovirus expression. Also different signals for posttranslational modification recognized by insect cells are known in the art.

The present invention also relates to a host cell transformed with a recombinant vector as defined above.

The present invention also relates to antibodies that are specifically raised against the peptides of the present invention, preferably against those peptides wherein the arginines that precede a glycine residue are methylated. These antibodies may be polyclonal or monoclonal. To prepare antibodies a host animal is immunized using the peptides of the present invention in a pharmaceutically acceptable carrier, wherein at least one of the arginines that precede a glycine residue of said peptides is methylated. Pharmaceutically acceptable carriers include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers; and inactive virus particles. Such carriers are well known to those of ordinary skill in the art.

Preferred adjuvants to enhance effectiveness of the composition include, but are not limited to: aluminum hydroxide (alum), N-acetyl-muramyl-L-threonyl-D-isoglutamine (thr-MDP) as found in U.S. Pat. No. 4,606,918, N-acetylnormuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE) and RIBI, which contains three components extracted from bacteria, monophosphoryl lipid A, trehalose dimycolate, and cell wall skeleton (MPL+TDM+CWS) in a 2% squalene/Tween 80 emulsion. Any of the 3 components MPL, TDM or CWS may also be used alone or combined 2 by 2. Additionally, adjuvants such as Stimulon (Cambridge Bioscience, Worcester, Mass.) or SAF-1 (Syntex) may be used. Further, Complete Freund's Adjuvant (CFA) and Incomplete Freund's Adjuvant (IFA) may be used for non-human applications and research purposes.

The immunogenic compositions typically will contain pharmaceutically acceptable vehicles, such as water, saline, glycerol, ethanol, etc. Additionally, auxiliary substances, such as wetting or emulsifying agents, pH buffering substances, preservatives, and the like, may be included in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect. The proteins may also be incorporated into Immune Stimulating Complexes together with saponins, for example Quil A (ISCOMS).

Immunogenic compositions used to raise antibodies comprise a 'sufficient amount' or 'an immunologically effective amount' of the peptides of the present invention, as well as any other of the above mentioned components, as needed. 'Immunologically effective amount', means that the administration of that amount to an individual, either in a single dose or as part of a series, is effective to provoke an immune response and to raise antibodies, as defined above. This amount varies depending upon the health and physical condition of the individual, the taxonomic group of the individual to be treated (e.g. nonhuman primate, primate, rabbit, etc.), the capacity of the individual's immune system to synthesize antibodies, the immunogenicity of the antigenic peptide, and its mode of administration, and other relevant factors. It is expected that the amount will fall in a relatively broad range that can be determined through routine trials. Usually, the amount will vary from 0.01 to 1000 $\mu$g/dose, more particularly from 0.1 to 100 $\mu$g/dose.

The immunogenic compositions are conventionally administered parenterally, typically by injection, for example, subcutaneously or intramuscularly. Additional formulations suitable for other methods of administration include oral formulations and suppositories. Dosage treatment may be a single dose schedule or a multiple dose schedule. The vaccine may be administered in conjunction with other immunoregulatory agents.

The host serum or plasma is collected following an appropriate time interval to provide a composition comprising antibodies reactive with the peptides of the present invention. The gamma globulin fraction or the IgG antibodies can be obtained, for example, by use of saturated ammonium sulfate or DEAE Sephadex, or other techniques known to those skilled in the art. The antibodies are substantially free of many of the adverse side effects which may be associated with other anti-viral agents such as drugs, for the treatment of infectious, chronic, or recurrent mononucleosis. Such antibodies may also be used to diagnose certain diseases, such as Burkitt's lymphoma, wherein Epstein-Barr virus has been implicated.

The term 'immunogenic' refers to the ability of a substance to cause a humoral and/or cellular response, whether alone or when linked to a carrier, in the presence or absence of an adjuvant.

The antibodies of the claimed invention may also be monoclonals that are prepared with said antibody being specifically reactive with any of said peptides, and with said antibody being preferably a monoclonal antibody.

The monoclonal antibodies of the invention can be produced by any hybridoma liable to be formed according to classical methods from splenic cells of an animal, particularly from a mouse or rat, immunized against the claimed peptides of the present invention on the one hand, and of cells of a myeloma cell line on the other hand, and to be selected by the ability of the hybridoma to produce the monoclonal antibodies recognizing the methylated forms of the peptides which has been initially used for the immunization of the animals.

The antibodies involved in the invention can be labelled by an appropriate label of the enzymatic, fluorescent, or radioactive type.

The monoclonal antibodies according to this preferred embodiment of the invention may be humanized versions of mouse monoclonal antibodies made by means of recombinant DNA technology, departing from parts of mouse and/or human genomic DNA sequences coding for H and L chains or from cDNA clones coding for H and L chains.

Alternatively the monoclonal antibodies according to this preferred embodiment of the invention may be human monoclonal antibodies. These antibodies according to the present embodiment of the invention can also be derived from human peripheral blood lymphocytes of patients with SLE or any other autoimmune disease or with infectious, or recurrent or chronic mononucleosis. Such human monoclonal antibodies are prepared, for instance, by means of human peripheral blood lymphocytes (PBL) repopulation of severe combined immune deficiency (SCID) mice (for recent review, see Duchosal et al. 1992) or by screening Epstein Barr-virus-transformed lymphocytes of infected or vaccinated individuals for the presence of reactive B-cells by means of the antigens of the present invention.

The present invention also relates to the anti-idiotype antibodies that are raised upon immunization with an antibody as defined above and that specifically react with said antibodies, thereby mimicking the peptides of the present invention. The methods for production of monoclonal anti-idiotype antibodies, which are well known in the art, have been described, for instance, by Gheuens et MacFarlin (1982).

The present invention also relates to truncated versions or single chain versions of the antibodies and anti-idiotype antibodies as defined above, that have retained their original specificity for reacting with the antigens.

The present invention also relates to proteins or peptides that mimic the antibodies as defined above such as microproteins as can be obtained by phage display or the highly variable domain of a recombinant antibody as obtained by screening upon repertoire cloning.

The present invention also relates to a method for detecting antibodies that specifically react with the peptides or anti-idiotype antibodies of the present invention, present in a biological sample, comprising: (i) contacting the biological sample to be analysed for the presence of said antibodies with a peptide or anti-idiotype antibody as defined above, (ii) detecting the immunological complex formed between said antibodies and said peptide or anti-idiotype antibody.

The present invention also relates to a reverse method for detecting the peptides and/or the anti-idiotype antibodies of the present invention with antibodies present in a biological sample that specifically react with methylated forms of said peptides and/or anti-idiotype antibodies that mimic such peptides, comprising: (i) contacting the biological sample to be analysed for the presence of said peptides or anti-idiotype antibodies with the antibodies as defined above, (ii) detecting the immunological complex formed between said antibodies and said peptide or anti-idiotype antibody. The methods as defined above, can be used in the diagnosis of autoimmune diseases such as systemic lupus erythematosus, discoid lupus erythematosus, scleroderma, dermatomyositis, rheumatoid arthritis, Sjögren's syndrome, or diseases in which Epstein-Barr virus can be implicated such as infectious, recurrent or chronic mononucleosis, or Burkitt's lymphoma, or nasopharyngeal carcinoma, or Hodgkin's disease, or of certain cancers such as Ewing sarcoma, or malignant melanoma of soft tissue.

According to a specific embodiment, the present invention relates to the development of a diagnostic technique that allows differentiation between those autoimmune diseases in which the characteristic antibodies often crossreact with the same antigen, thus resulting in difficult and slow diagnosis. Such diagnostic technique can be obtained by the simultaneous use of several antigens, methylated and unmethylated, and at least two epitopes, a methylated and a non-methylated form of any of the claimed peptides and/or anti-idiotype antibodies of the present invention.

The present invention also relates to a diagnostic kit for use in detecting the presence of said antibodies, said kit comprising at least one peptide or anti-idiotype antibody or microprotein as defined above, with said peptide or anti-idiotype antibody or microprotein being preferably bound to a solid support.

The present invention also relates to a diagnostic kit for determining the type of autoimmune disease or the type of infection or to characterize certain cancers, said kit comprising at least one peptide or anti-idiotype antibody or microprotein as defined above, with said peptide or anti-idiotype antibody or microprotein being preferably bound to a solid support.

The present invention also relates to a diagnostic kit as defined above, said kit comprising a range of said peptides and/or anti-idiotype antibodies or microprotein which are attached to specific locations on a solid substrate.

The present invention also relates to a diagnostic kit as defined above, wherein said solid support is a membrane strip and said peptides and/or anti-idiotype antibodies or microproteins are coupled to the membrane in the form of parallel lines.

The immunoassay methods according to the present invention may utilize for instance single or specific oligomeric antigens, dimeric antigens, as well as combinations of single or specific oligomeric antigens. The peptides of the present invention may be employed in virtually any assay format that employs a known antigen to detect antibodies that characterize a certain disease or infection. A common feature of all of these assays is that the antigenic peptide or anti-idiotype antibody or microprotein is contacted with the body component suspected of containing the antibodies under conditions that permit the antigen to bind to any such antibody present in the component. Such conditions will typically be physiologic temperature, pH and ionic strength using an excess of antigen. The incubation of the antigen with the specimen is followed by detection of immune complexes comprised of the antigen.

Design of the immunoassays is subject to a great deal of variation, and many formats are known in the art. Protocols may, for example, use solid supports, or immunoprecipitation. Most assays involve the use of labelled antibody or peptide; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labelled and mediated immunoassays, such as ELISA assays.

The immunoassay may be, without limitation, in a heterogeneous or in a homogeneous format, and of a standard or competitive type. In a heterogeneous format, the peptide or anti-idiotype antibody or microprotein is typically bound to a solid matrix or support to facilitate separation of the sample from the peptide or anti-idiotype antibody or microprotein after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidene fluoride (known as Immunolon™), diazotized paper, nylon membranes, activated beads, and Protein A beads. For example, Dynatech Immunolon™1 or Immunolon™2 microtiter plates or 0.25 inch polystyrene beads (Precision Plastic Ball) can be used in the heterogeneous format. The solid support containing the antigenic peptides or anti-idiotype antibodies or microprotein is typically washed after separating it from the test sample, and prior to detection of bound antibodies. Both standard and competitive formats are know in the art.

In a homogeneous format, the test sample is incubated with the combination of antigens in solution. For example, it may be under conditions that will precipitate any antigen-antibody or anti-idiotype antibody-antibody or microprotein-antibody complexes which are formed. Both standard and competitive formats for these assays are known in the art. For instance, to characterize SLE or systemic lupus erythematosus in a standard format, the amount of SLE-antibodies in the antibody-antigen complexes is directly monitored. This may be accomplished by determining whether a second type of labelled anti-xenogenetic (e.g. anti-human) antibodies which recognize an epitope on the first type of SLE-antibodies will bind due to complex formation. In a competitive format, the amount of SLE-antibodies in the sample is deduced by monitoring the competitive effect on the binding of a known amount of labelled antibody (or other competing ligand) in the complex. The detection of SLE-antibodies for diagnosis of SLE is used as an illustration. Wherever the term "SLE-antibodies" is used throughout the specification, this should not be considered as limitative. Like wise, the other autoimmune diseases are diagnosed by detection of other antibodies, and mononucleosis is diagnosed by detection of anti-Epstein-Barr virus antibodies.

Complexes formed comprising SLE-antibody (or in the case of competitive assays, the amount of competing antibody) are detected by any of a number of known techniques, depending on the format. For example, unlabelled SLE-antibodies in the complex may be detected using a conjugate of anti-xenogenetic Ig complexed with a label (e.g. an enzyme label).

In an immunoprecipitation or agglutination assay format the reaction between the SLE-antigens and the SLE-antibody forms a network that precipitates from the solution or suspension and forms a visible layer or film of precipitate. If no SLE-antibody is present in the test specimen, no visible precipitate is formed.

Currently, there exist three specific types of particle agglutination (PA) assays. These assays are used for the detection of antibodies to various antigens when coated to a support. One type of this assay is the hemagglutination assay using red blood cells (RBCs) that are sensitized by passively adsorbing antigen (or antibody) to the RBC. The addition of specific antigen antibodies present in the body component, if any, causes the RBCs coated with the purified antigen to agglutinate.

To eliminate potential non-specific reactions in the hemagglutination assay, two artificial carriers may be used instead of RBC in the PA. The most common of these are latex particles. However, gelatin particles may also be used. The assays utilizing either of these carriers are based on passive agglutination of the particles coated with purified antigens.

The antigenic peptides of the present invention will typically be packaged in the form of a kit for use in these immunoassays. The kit will normally contain in separate containers the antigenic peptide or anti-idiotype antibody, control antibody formulations (positive and/or negative), labelled antibody when the assay format requires the same and signal generating reagents (e.g. enzyme substrate) if the label does not generate a signal directly. The antigenic peptide or anti-idiotype antibody may be already bound to a solid matrix or separate with reagents for binding it to the matrix. Instructions (e.g. written, tape, CD-ROM, etc.) for carrying out the assay usually will be included in the kit.

The solid phase selected can include polymeric or glass beads, Hi nitrocellulose, microparticles, microwells of a reaction tray, test tubes and magnetic beads. The signal generating compound can include an enzyme, a luminescent compound, a chromogen, a radioactive element and a chemiluminescent compound. Examples of enzymes include alkaline phosphatase, horseradish peroxidase and beta-galactosidase. Examples of enhancer compounds include biotin, anti-biotin and avidin. Examples of enhancer compounds binding members include biotin, anti-biotin and avidin. In order to block the effects of rheumatoid factor-like substances, the test sample is subjected to conditions sufficient to block the effect of rheumatoid factor-like substances. These conditions comprise contacting the test sample with a quantity of for instance anti-human IgG to form a mixture, and incubating the mixture for a time and under conditions sufficient to form a reaction mixture product substantially free of rheumatoid factor-like substance.

The present invention particularly relates to an immunoassay format in which several peptides of the invention are coupled to a membrane in the form of parallel lines. This assay format is particularly advantageous for allowing a discrimination between the separate autoimmune diseases. The antigens that are immobilized on the membrane will preferentially be the methylated and unmethylated form of poly(Arg-Gly), combined with native and thus methylated SmD1 and/or SmD3 and/or Sm69, and unmethylated, recombinant SmD1 and/or SmD3 and/or Sm69.

EXAMPLES

Example 1

Sera

Sm positive sera were obtained from the Department of Rheumatology of the University clinic in Ghent, Belgium (Dr. De Keyser and Dr. Veys). These sera were identified by microgel diffusion blotting (MDB) using rabbit thymus extract (Zeus, Bayer, Raritan, USA) as substrate (De Keyser et al., 1990). The Sm-positivity was defined by a positive immunoreaction at the same molecular weight position (approx. 14 kDa) as the α-SmD reference serum.

Example 2

Isolation of native SmD

The snRNP particles are purified from HeLa nuclear extracts by immuno affinity chromatography (R. Lührmann, Marburg, Germany).

The snRNP particles are received in 20 mM Hepes/KOH, pH 7.9–250 à 420 mM NaCl—5% glycerol—1.5M $MgCl_2$—0.2 mM EDTA—0.5 mM DTE—0.5 mM PMSF. SmD is isolated from these particles as described by Lehmeier et al. (1990) with some modifications. Briefly, in a first step, snRNPs are concentrated in a centricon concentrator (30K centripep, Amicon) to a final volume of 5–10 mg/ml. Subsequently, the snRNPs are dissolved in Laemmli sample buffer, separated in a preparative 15% Laemmli gel (1 cm thick, 14 cm well; protein load 3 mg) and stained with Coomassie Brilliant Blue.

The 14 kDa SmD (containing SmD1, SmD2 and SmD3) band is cut from the gel, rinsed in water and cut into 1 $mm^3$ cubes. Proteins are eluted from the polyacrylamide gel in the BioRad apparatus according to the manufacture's instructions. Residual SDS and CoomassieBB are removed from the electroeluted proteins by ion-pair extraction (precipitation of the dried protein with aceton/acidic acid/triethylamine/water:85/5/5/5). The pellet is dissolved in 6M ureum, 0.1 M acetic acid (glacial) and immediately neutralized with 1.5 M Tris-HCl. Protein concentration is determined by MicroBCA method (Pierce,USA), an average yield of 80 $\mu g$ SmD/mg snRNPs is obtained.

Example 3

Expression of SmD1 as short mTNF-fusion in E. coli and purification of the fusion protein.

The SmD1 coding sequence (357 bp) was isolated from a cDNA clone bought from Organon Technika as a 367 bp PCR fragment by using pfu polymerase (Tm: 55° C.). This PCR fragment was cut with BamHI and XbaI and inserted into the BamHI/XbaI cut expression vector pIGFH111. This expression vector was transformed to E. coli expression strain SG4044(pcI857). Induction of this vector/strain combination at 37° C. showed a strong signal of ±18 kDa on CBB stained gels and on Western blot. Upon localisation analysis the protein proved to be present in the soluble fraction. No significant proteolytic breakdown could be observed. Bacterial cells derived from three liter culture were suspended in lysis buffer (10 mM Tris- 100 mM KCl pH 6.8) until 3 times the amount of wet cells. Prior to lysis by French press, ε-aminocaproic acid, DTT, and PMSF were added to a final concentration of 25 mM, 1 mM and 2 mM respectively. The cell suspension was forced twice through the French press and pressure was kept at 14000 psi. Before centrifugation, the lysate was diluted with lysis buffer (5 times the wet cell weight) and was centrifuged for 20 minutes at 27,000 g at 4° C. Guanidine HCl was added to the supernatant to an end concentration of 4.5 M. The recombinant fusion protein, containing a His-tag, was purified in a single step by metal affinity chromatography (Ni-IMAC sepharose). Chromatography was performed at room temperature. The column was loaded with 1 column volume of $NiCl_2$ (5 mg/ml), washed with water and equilibrated with buffer A (6 M guanidine HCl, 0.1 M sodium phosphate, 0.05% TritonX100, pH 6.5). The proteins were loaded on $Ni^{2+}$ chelating sepharose (Pharmacia, Sweden; approx. 18 mg protein/ml gel) and the column was washed with 4 bed volumes of buffer A. SmD1 was eluted with a linear gradient of buffer B (6 M guanidine HCl, 0.1 M sodium phosphate, 0.05% TritonX100, pH 3.5) and the protein eluted between 70% and 90% buffer B.

Example 4

Figures 2A, 2B:
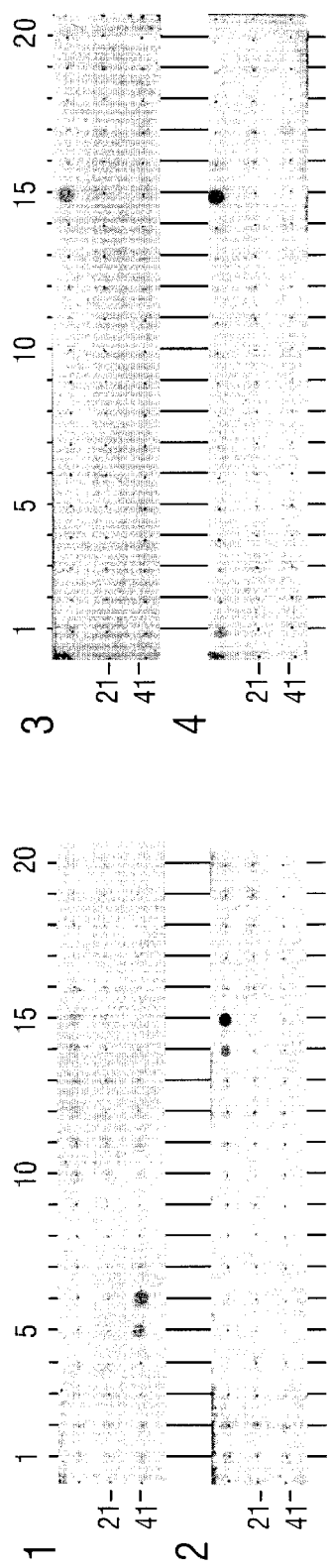
FIG. 2: Immunodot of HPLC fractions with 5 patients sera and 1 control serum.

Expression of SmD1 as short mTNF-fusion in the baculoviral system and purification of the fusion protein The cDNA gene coding for the mTNF-His6-hSmD fusion protein was isolated from the bacterial expression plasmid pIGFH 111 hSmD (see example 3) as a 520 bp DraI-XbaI fragment, and inserted in the BamHI (filled in)-XbaI opened baculo transfer plasmid pVL1393, resulting in the recombinant transfer plasmid pVLTNFH6hSmD (see FIG. 2). The fusion gene is here under transcriptional control of the baculovirus strong polyhedrin promoter. The pVmTNFH6hSmD1 baculo transfervector was used to generate recombinant mTNF-His6-hSmD1 baculovirus following the baculogold transfection approach (Pharmingen, San Diego, USA). Infection of Spodoptera frugiperda cells (Sf9) with the recombinant virus resulted in the expression of a 18 kDa protein which was recognized on Western blot by a monoclonal antibody specific for SmD (Progen, Heidelberg, Germany, data not shown). Using the cell lysate for testing the specificity of different human sera was not feasible since a high aspecific background reaction of the human sera with baculoviral proteins masked possible specific SmD recognition. The SmD fusion protein was therefore purified by Ni-IMAC purification as described previously with one adaptation: following french press, the cell lysate was precipitated and redissolved in buffer A (see example 3).

Example 5

Sequence and mass analysis of natural, E. coli, and baculoviral SmD1

Natural SmD electroeluted from HeLa nuclear extracts immobilized on a PVDF membrane in a ProSpin device (Perkin Elmer, California, USA) was subjected to endoLys-C digestion to obtain detailed sequencing data of internal peptides. The membrane was incubated with 100 mM Tris pH 8.2, 1% hydrogenated TritonX-100, 1 mM $K_3$-EDTA, 10% acetonitrile and 0.5 μg enzyme. The digestion was performed overnight at 37° C. The peptide mixture was separated on a C4 Vydac HPLC-column (using a gradient of 10–70% solvent B: 70% acetonitrile/0.1% TFA) and a flow rate of 0.2 ml/min. The eluted peptide peaks were manually recovered. In the C-terminal 25-mer peptide of SmD1 nine dimethylarginine residues were sequenced, only the last two arginines were unmodified. The position of $N^G,N^G$-dimethylarginine in the sequence chromatogram was confirmed by applying the pure modified amino acid (Sigma, St Louis, USA) as standard. This modification was absent in recombinant SmD1 from E. coli (revealed in the course of sequencing peptides generated by endo-GluC) implying that the modification, resulting from the action of methyltransferase, does not occur in E. coli.

This conclusion was confirmed by mass analysis of E. coli recombinant SmD1. This protein, eluting in a single peak upon reversed-phase chromatography, was analysed by electrospray on a Bio-Q quadrupole mass spectrometer equipped with an electrospray ion source (Fisons). Ten μl of the sample solution containing 20 pmol in 50% acetonitrile-1% acetic acid was analysed. Calibration of the scans was performed with 50 pmol horse heart myoglobin. The sample contained 3 masses: 17,435 Da, 17,305 Da, and 16,992 Da corresponding respectively to the full size protein, the protein without the N-terminal methionine, and the protein lacking the N-terminal Met and the C-terminal Arg-Arg. From these results, it can be concluded that the purified E. coli recombinant SmD1 is the intact, unmodified molecule and that the lack of specific immunoreactivity of the recombinant SmD1 is not due to loss of the C-terminus.

Mass analysis of baculoviral recombinant SmD1 showed a heterogeneous result: one of the major mass peaks (17,297 Da) could be assigned to the unmodified protein lacking the N-terminal methionine while within the minor peaks masses of 17,629 and 17,711 could be tentatively assigned to the presence of 7 and 10 dimethylarginines.

Example 6

Epitope mapping of baculo SmD1

Baculo SmD1 fusion protein was digested with EndoGlu-C as follows: 300 μg TCA-precipitated protein was dissolved in 50 μl 100 mM $NH_4$-acetate buffer pH 4.3. The EndoGlu-C enzyme (Boehringer, Mannheim, Germany) was added at a ratio of 1/100 and the mixture was incubated overnight at 26° C. The digest was subsequently vacuum dried (SpeedVac), redissolved in 0.1% TFA–20% acetic acid and the peptides were separated on a reversed-phase HPLC column ($C_4$-Vydac). Peptide peaks were manually recovered. A similar approach was followed for EndoLys-C (Boehringer, Mannheim, Germany) digestion of baculo SmD1 with the following modifications:the protein is dissolved in 50 μl 100 mM Tris-HCl, pH 8, 10% acetonitrile, 10 mM $K_3$EDTA, and enzyme is added at a ratio of 1/120.

The HPLC fractions were vacuum dried and dissolved in 10% acetonitrile, 50 mM carbonate buffer pH 9.6. From each fraction 2 μl was spotted on ABC nylon membrane (Pall, N.Y.). After spotting, the membranes were blocked for 1 hour in 0.5% caseine in PBS to which 0.1% 0.25 glycine is added. Subsequently, the membranes are incubated overnight with serum (1/100) in 0.5% caseïne in PBS supplemented with Triton X705 and 2.03 g/L $MgCl_2.6H_2O$. The membranes were washed 3 times for 3 min. in PBS, 0.05% Tween20 and incubated with anti-human IgG (1/8000) conjugated with alkaline phophatase. The immune reaction was visualized by adding NBT/BCIP in a 1/500 dilution.

The endoGlu-C derived fractions were incubated with one positive serum and one control serum. A strong immunoreaction was revealed with fraction 17. Sequencing of fraction 15 learned that this fraction contained the C-terminal peptide in which the RG motif is dimethylated. Mass analysis of fraction 8 showed that this fraction contained the C-terminal peptide without the modified arginines. Analysis of the fractions located between 8 and 17 indicated that these fractions contain the C-terminal peptide in which the 5 final RG motifs are dimethylated while and the first 4 RG motifs are partially monomethylated. This can be concluded from a mass difference of 14 between the fractions.

The EndoLys-C derived fractions (FIG. 1) were incubated separately with 6 positive sera and one control serum. In 5 out of 6 positive sera, a signal significantly higher than the control serum was limited to fraction 15 which was identified both by sequencing and mass analysis as the C-terminal peptide with dimethylargines. Again, mass analysis indicated that the fractions 8 to 14 correspond to the non-methylated and less methylated forms of the C-terminal peptide.

Figure 3:
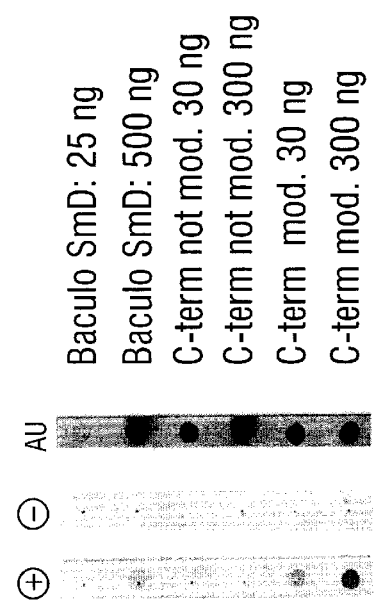
FIG. 3: Immunodot of the C-terminal peptide (C-term mod) and without (C-term nt mod) dimethylarginine, and of the recombinant (baculo SmD, coli SmD) and natural protein (native). Strips were incubated with a anti-SmD positive serum (+) and a control serum (−). Total protein staining (Aurodyne) was performed on the third strip.
Figure 4:
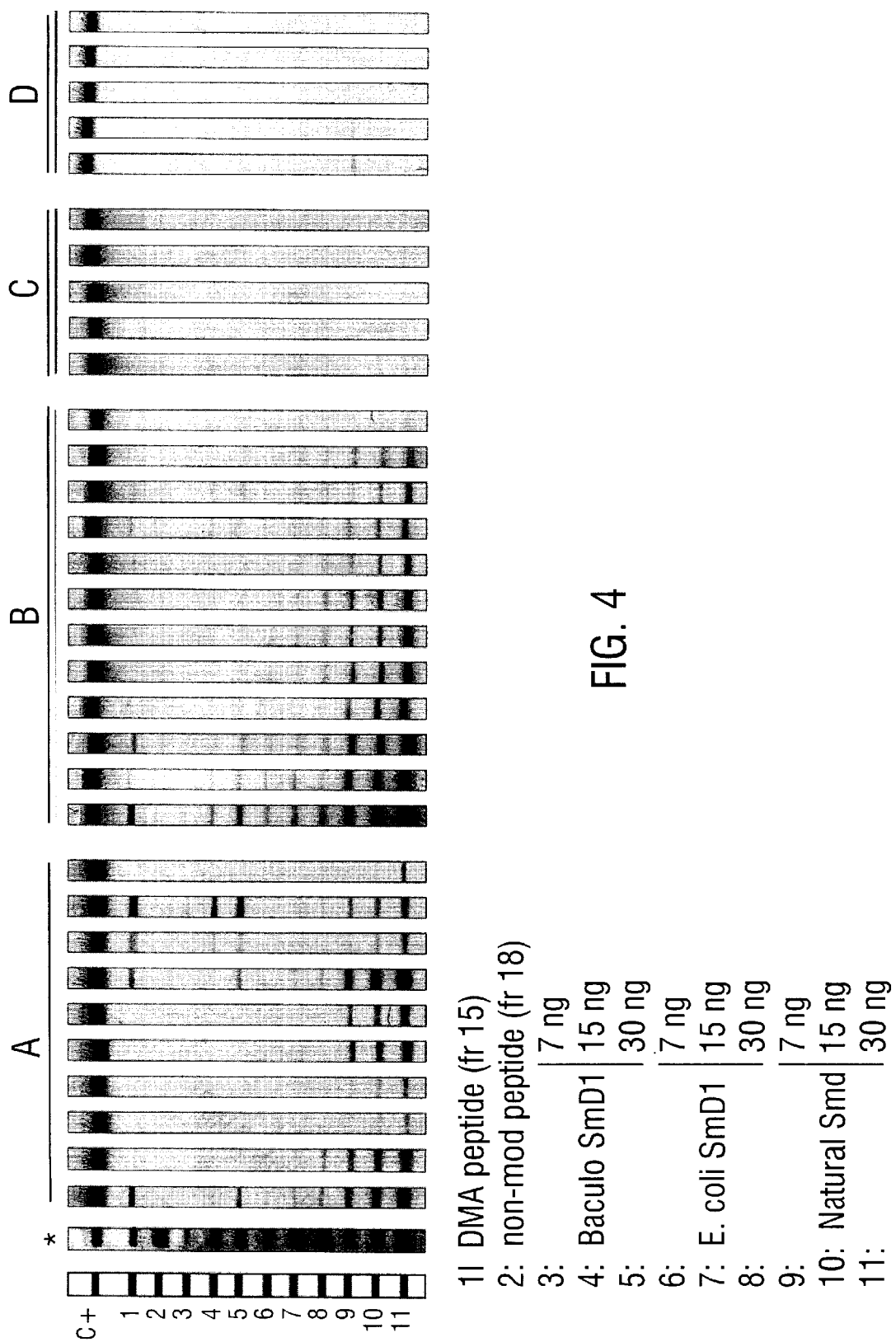
FIG. 4: LIA with modified (dimethyl arginine) C terminal peptide (fraction 15 from EndoLys-C digest, line 1 on the strip), and non-modified C terminal peptide (fraction 8 from the EndoLys-C digest, line 2 on the strip), both applied in equal amounts (60 ng). Additionally, 7, 15 and 30 ng of recombinant SmD1 from baculovirus- or E. Coli-infected insect cells (resp. 4,5,6 and 7,8,9) as well as 15 and 30 ng of a mixture of gel-purified SmD (native) were applied to the strips. The total protein staining (Aurodyne) was performed on the first strip. The strips were incubated with (A) a panel of anti-SmD positive sera selected by INNO-LIA ANA from ANF-positive sera, (B) a panel of anti-SmD positive sera selected by INNO-LIA ANA from a cohort of SLE patients diagnosed according to the ACR criteria, (C) sera selected from MCTD patients (control panel) and (D) sera selected from ANF- negative sera (control panel). No reactivity was observed with sera from the control panels.

These results were confirmed by isolating selectively the non-modified and the modified peptide from a preparative endoLys-C digest of baculo SmD1. In FIG. 1 it can be seen that fraction 8 with the non-modified SmD1 peptide contained less material than fraction 15 with the dimethylated peptide. It is therefore possible that the exclusive reactivity of the modified peptide was due to different amounts of modified and non-modified peptide being transferred in the dot-blot experiment (FIG. 2). To exclude such quantitative variations, the peptides were analysed in a dot spot experiment as described. However, in this experiment equal quantities (based on BCA protein determination) of both peptides, modified and non-modified peptide, were applied. For comparison, the total natural SmD, the total recombinant E. coli and baculoviral SmD1 were applied in comparable amounts in the immunodot (FIG. 3). Finally peptides were applied in a line immunoassay experiment (Polet et al., Clinical Chemistry, 37, 1991) (FIG. 4). Again equal amounts (60 ng) of modified and non-modified SmD1 peptides were applied to a nylon membrane. The amount of peptide bound was visualized by protein colloidal staining (Aurodye, Amersham, Buckinghamshire, UK; FIG. 4). Additionally, 30,15 and 7 ng of recombinant SmD1 from E.coli- or baculovirus-infected insect cells as well as a mixture of gel-purified SmD1, SmD2 and SmD3 were applied to the strips. These were then tested with 21 anti-Sm patient sera that were immunoreactive to a mixture of HeLa SmD1, SmD2 and SmD3. Six (29%) of these anti-Sm patient sera gave significant signals with the modified peptide D1, while the non-modified peptide reacted with none of the 21 tested sera. An independent set of anti-Sm Brazilian sera (n=93) showed a comparable rate of reactivity with the modified peptide (4/14 anti-Sm sera; 29%). These experiments substantiate our hypothesis that there are at least 2 epitopes involved in the immunoreactivity of natural SmD: one epitope is present is the total E. coli recombinant SmD molecule while an additional epitope is located in the C-terminus (90–119) of the SmD1 molecule. The presence of dimethylarginines in this peptide is crucial for recognition by patient sera.

References

Andersen, J., Feeney, R. J. and Zieve, G. W. 1990. Identification and characterization of the small nuclear ribonucleoprotein particle D' core protein. Mol.Cell.Biol. 10, 4480–4485

Barakat, S., Briand, J. -P., Weber, J. -C., Van Regenmortel, M. H. V. and Muller,S. 1990. Recognition of synthetic peptides of Sm-D autoantigen by lupus sera. Clin.exp.Immunol. 81, 256–262

De Keyser, F. G., Verbruggen, G., Veys, E. M., Nimmegeers, J., Schatteman, L., Goethals, K., Vandenbossche, M. 1990. "Microgel Diffusionblotting" for sensitive detection of antibodies to extractable nuclear antigens. Clin.Chem. 36, 337–339

Gheuens, J., MacFarlin, D. 1982. Use of monoclonal anti-idiotypic antibody to P3-X63Ag8 myeloma protein for analysis and purification of B lymphocyte hybridoma products. Eur.J.Immunol. 12, 701–703

Hoch, S. O. 1989. Application of protein blotting in the study of autoimmunedisease. In *Manual of Biological Markers of Disease* B2.4:1–29, Kluwer, Netherlands Weiner, H. L. 1997. Oral tolerance for the treatment of autoimmune diseases. Annu.Rev.Med. 48, 341–351

James, J. A., Mamula, M. J. and Harley, J. B. 1994. Sequential autoantigenic determinants of the small nuclear ribonucleoprotein Sm D shared by human lupus autoantibodies and MRL lpr/lpr antibodies. Clin.Exp.Immunol. 98, 419–426

Lehmeier, T., Foulaki, K. And Lührman, R. 1990. Evidence for three distinct D proteins, which react differentially with anti-Sm autoantibodies, in the cores of the major snRNPs U1, U2, U4/U6 and U5. Nucleic Acids Res 18, 6475–6484

Najbauer, J., Johnson, B. A., Young, A. L. and Aswad, D. W. 1993. Peptides with sequences similar to glycine arginine rich motifs in proteins interacting with RNA are efficiently recognized by methyltransferases modifying arginine in numerous proteins. J.Biol.Chem. 268, 10501–10509

Rajpurohit, R., Lee, S. O., Park, J. O., Paik, W. K. and Kim, S. 1994. Enzymatic methylation of recombinant heterogeneous nuclear RNP protein A1. J.Biol.Chem. 269, 1075–1082

Rawal, N., Rajpurohit, R., Lischwe, M. A., Williams, K., R;, Paik, W., K., Kim, S. 1995. Structural specificity of substrate for S-Adenosylmethionine:protein arginine N-methyltransferases. Biochem.Biophys.Acta, 1248, 11–18

Rivkin, E., Vella, M. J. and Lahita, R. G. 1994. A heterogeneous immune response to an Sm-D-like epitope by SLE patients. J.Autoimmun. 7, 119–132

Rokeach, L. A., Haselby, J. A and Hoch, S. O. 1988. Molecular cloning of a cDNA encoding the human Sm-D autoantigen. Proc.Natl.Acad.Sci.USA, 85, 4832–4836

Rokeach, L. A., Haselby, J. A. and Hoch, S. O. 1992a. Overproduction of a human OsnRNP)-associated Sm-D autoantigen in *Escherichia coli* and *Saccharomyces cerevisiae*. Gene 118, 247–253

Rokeach, L. A., Jannatipour, M., Haselby, J. A. and Hoch, S. O. 1992b. Mapping of the immunoreactive domains of a small nuclear ribonucleiprotein-associated Sm-D autoantigen. Clin.lmmunol.Immunopath. 35, 315–324

Sabbatini, A., Dolcher, M. P., Marchini, B., Bombardieri, S. And Migliorini, P. 1993a. Mapping of epitopes on the SmD molecule: the use of multiple antigen poepotides to measure autoantibodies in systemlic lupus erythematosus. J. Rheumatol. 20,1679–1683

Sabbatini, A., Bombardieri, S. And Migliorini, P. 1993b. Autoantibodies from patients with systemic lupus erythematosus bind a shared sequence of SmD and Epstein-Barr virus-encoded nuclear antigen EBNA I. Eur.J.Immunol. 23, 1146–1152

Van Venrooij, W. J., P. Charles and R. N. Maini 1991. The conscensus workshops for the detection of autoantibodies to intrzcellular antigens in rheumatic diseases. J. Immunol. Methods, 140, 181–189

Wagatsuma, M., Asami, N., Miyachi, J., Uchida, S., Watanabe, H. and Amann, E. 1993. Antibody recognition of the recombinant human nuclear antigens RNP 70 kD, Sm-A, Sm-B and Sm-D by autoimmune sera. Mol.Immunol. 30, 1491–1498

What is claimed is:

1. A Peptide containing less than 50 amino acids, comprising at least one dimer of the type XG, wherein X stands for a $N^G$-mono- or $N^G$-$N^G$-dimethylated arginine, asymmetrical dimethyl arginine, or $N^G$-$N^G$-dimethylated arginine, symmetrical dimethyl arginine, that is specifically recognized by antibodies present in sera from patients with systemic lupus erythematosus (SLE), and wherein said antibodies are specifically associated with SLE; and with said methylation being crucial for the recognition of the peptide by said antibodies.

2. The peptide according to claim 1 comprising the amino acid sequence of SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15 or, an analog of any of SEQ ID NO 1–15, wherein the analog has an amino acid sequence identical to the respective SEQ ID NO except that the analog comprises conservative amino acid substitutions at one or more positions, where the conservative amino acid substitutions are selected from the following: Thr, Gly, or Asn substituted for Ser; His, Lys, Glu, or Gln substituted for Arg; Ile, Met, Phe, Val, or Tyr substituted for Leu; Ala, Thr, or Gly substituted for Pro; Pro, Ser, Ala, Gly, His, or Gln substituted for Thr; Pro, Gly, or Thr substituted for Ala; Met, Ile, Tyr, Phe, or Leu substituted for Val; Ala, Thr, Pro, or Ser substituted for Gly; Met, Leu, Phe, Val, or Tyr substituted for Ile; Met, Tyr, Ile, Leu, Trp, or Val substituted for Phe; Phe, Trp, Met, Ile, Val, or Leu substituted for Tyr; Ser, Thr, or Met substituted for Cys; Gln, Arg, Lys, Glu, or Thr substituted for His; Glu, His, Lys, Asn, Thr, or Arg substituted for Gln; Asp, Ser, or Gln substituted for Asn; Arg, Glu, Gln, or His substituted for Lys; Asn, Glu, or Gln substituted for Asp; Gln, Asp, Lys, Asn, His or Arg substituted for Glu; and Ile, Leu, Phe, or Val substituted for Met.

3. The peptide of claim 1 fused to a linker molecule.

4. A peptide comprising tandem repeats of at least two of any of the peptides of claim 1.

5. A diagnostic kit for use in detecting antibodies which specifically bind SmD antigens said kit comprising at least one peptide according to claim 1, with said peptide optionally bound to a solid support.

6. A diagnostic kit according to claim 5, said kit comprising at least one peptide according to claim 1, optionally in combination with native methylated SmD1 or SmD3 and recombinant unmethylated SmD1 or SmD3, wherein said peptides are attached to a solid substrate.

7. A diagnostic kit according to claim 5 wherein said solid support is a membrane strip.

8. The peptide according to claim 1 wherein X stands for $N^G$-mono- or $N^G$-$N^G$-dimethylated arginine.

9. The peptide according to claim 1 comprising the amino acid sequence of SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, or SEQ ID NO 15.

* * * * *

UNITED STATES PATENT AND TRADEMARK OFFICE
CERTIFICATE OF CORRECTION

PATENT NO. : 6,362,007 B1
DATED : March 26, 2002
INVENTOR(S) : Lydie Meheus, Ann Union, Joseph Raymackers and Reinhard Georg Lührmann It is certified that error appears in the above-identified patent and that said Letters Patent is hereby corrected as shown below:

Column 7,
Line 51, before the word "any" insert the word -- to --.

Column 10,
Line 11, delete "-presented" and insert -- presented -- therefor.

Column 11,
Line 47, delete "examples" and insert -- example -- therefor.

Column 12,
Line 3, delete "However," and insert -- However, -- therefor.

Column 14,
Line 46, delete "a mating" and insert -- α-mating -- therefor.

Column 19,
Line 67, delete "Hi".

Column 23,
Line 55, delete "30,15" and insert -- 30, 15 -- therefor.

Column 39,
Line 14, delete "$N^G\text{-}N^G$" and insert -- $N^G\text{-}N'^G$ -- therefor.

Signed and Sealed this

Eighteenth Day of June, 2002

*Attest:*

*Attesting Officer*

JAMES E. ROGAN
*Director of the United States Patent and Trademark Office*